(12) United States Patent
Katou et al.

(10) Patent No.: US 9,513,282 B2
(45) Date of Patent: Dec. 6, 2016

(54) SAMPLE ANALYZER, SAMPLE ANALYZING METHOD, AND SAMPLE ANALYZING SYSTEM

(71) Applicant: Sysmex Corporation, Kobe-shi (JP)

(72) Inventors: Takuma Katou, Kobe (JP); Daigo Fukuma, Kobe (JP); Yuichi Hamada, Kobe (JP)

(73) Assignee: Sysmex Corporation (JP)

( * ) Notice: Subject to any disclaimer, the term of this patent is extended or adjusted under 35 U.S.C. 154(b) by 258 days.

(21) Appl. No.: 13/785,703

(22) Filed: Mar. 5, 2013

(65) Prior Publication Data

US 2013/0262143 A1 Oct. 3, 2013

(30) Foreign Application Priority Data

Mar. 30, 2012 (JP) ................................. 2012-080322

(51) Int. Cl.
| | |
|---|---|
| *G01N 33/50* | (2006.01) |
| *G01N 33/80* | (2006.01) |
| *G01N 33/72* | (2006.01) |
| *G01N 35/00* | (2006.01) |
| *G01N 35/02* | (2006.01) |

(52) U.S. Cl.
CPC ........ *G01N 33/5094* (2013.01); *G01N 33/726* (2013.01); *G01N 33/80* (2013.01); *G01N 35/00603* (2013.01); *G01N 35/026* (2013.01)

(58) Field of Classification Search
None
See application file for complete search history.

(56) References Cited

U.S. PATENT DOCUMENTS

| | | | | |
|---|---|---|---|---|
| 6,099,469 | A  * | 8/2000 | Armstrong et al. | 600/300 |
| 2006/0153737 | A1* | 7/2006 | Saito et al. | 422/68.1 |
| 2006/0247866 | A1* | 11/2006 | Mishima et al. | 702/19 |
| 2007/0038406 | A1* | 2/2007 | Uemura et al. | 702/127 |
| 2007/0233518 | A1* | 10/2007 | Tanaka et al. | 705/2 |
| 2008/0071503 | A1* | 3/2008 | Fujita et al. | 702/188 |
| 2010/0105989 | A1  | 4/2010 | Inokuchi et al. | |

(Continued)

FOREIGN PATENT DOCUMENTS

| | | |
|---|---|---|
| CN | 101176114 A | 5/2008 |
| CN | 101334816 A | 12/2008 |

(Continued)

*Primary Examiner* — Fonya Long
*Assistant Examiner* — Gregory Lultschik
(74) *Attorney, Agent, or Firm* — Brinks Gilson & Lione

(57) ABSTRACT

Provided are a sample analyzer and sample analyzing method capable of performing proper and efficient analysis by fitting measurement items of a sample to the patient. A sample analyzer 1 obtains a patient ID and measurement order from a laboratory host 10 based on the sample ID read from a barcode label T1 of a sample container T via a barcode reader B1, and the measurement items of the obtained measurement order are recorded in a work list. The sample analyzer 1 also prepares revised measurement items based on past measurement results corresponding to the obtained patient ID. The sample analyzer 1 replaces the measurement items of the work list with the revised measurement items when the revised measurement items satisfy predetermined conditions, and measures and analyzes the sample according to the replacement measurement items.

21 Claims, 24 Drawing Sheets

(56) References Cited

U.S. PATENT DOCUMENTS

| | | | |
|---|---|---|---|
| 2010/0159603 | A1 | 6/2010 | Hamada et al. |
| 2011/0065193 | A1* | 3/2011 | Kitagawa et al. ............... 436/43 |
| 2011/0301976 | A1 | 12/2011 | Davis et al. |
| 2012/0248293 | A1 | 10/2012 | Yamazaki et al. |

FOREIGN PATENT DOCUMENTS

| | | | |
|---|---|---|---|
| CN | 101762713 A | 6/2010 | |
| CN | 102270274 A | 12/2011 | |
| JP | 05-119042 A | 5/1993 | |
| JP | H06-27118 A | 2/1994 | |
| JP | H08-50623 A | 2/1996 | |
| JP | 2005-98850 A | 4/2005 | |
| JP | 2006-275706 A | 10/2006 | |
| JP | 2007-322243 A | 12/2007 | |

\* cited by examiner

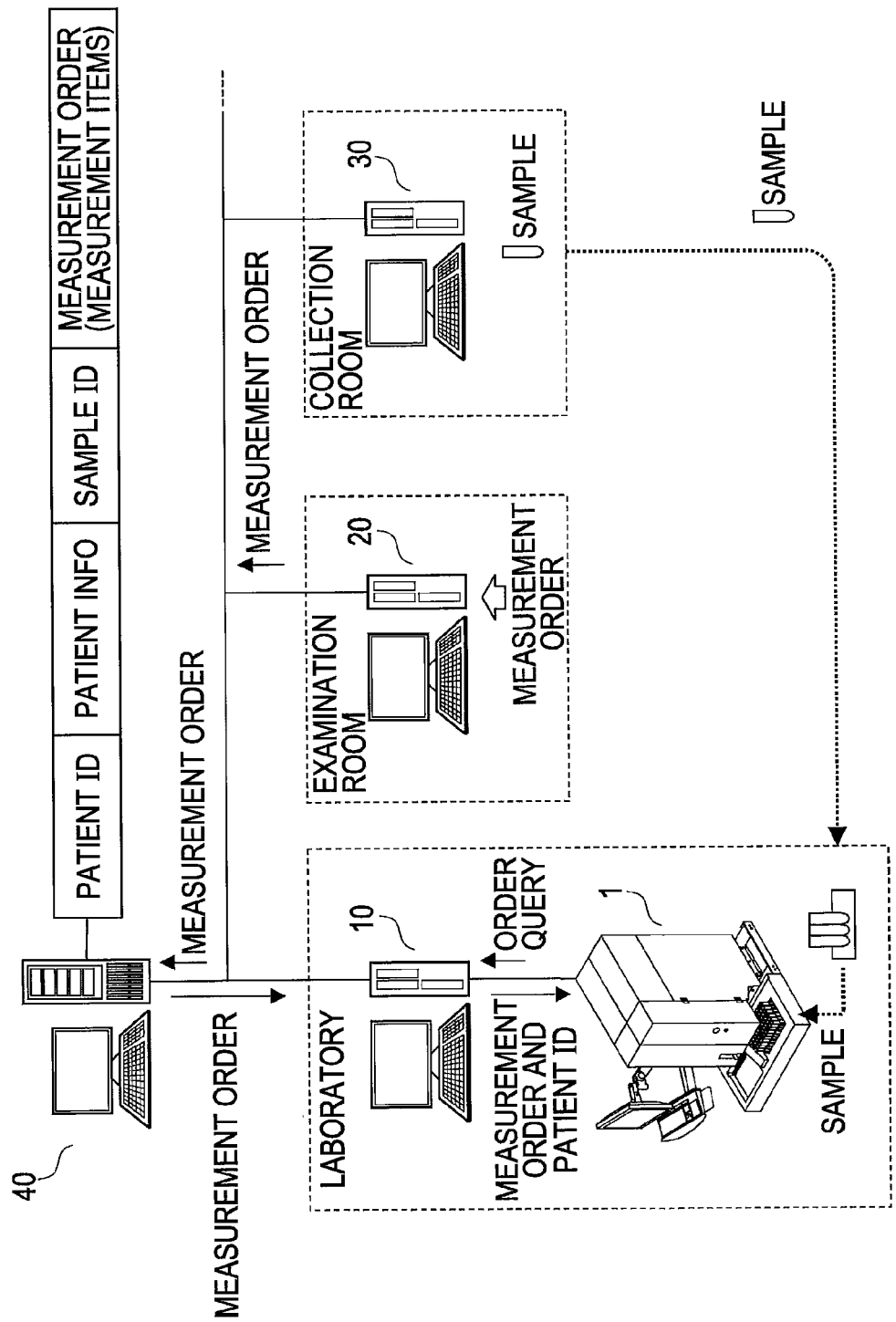

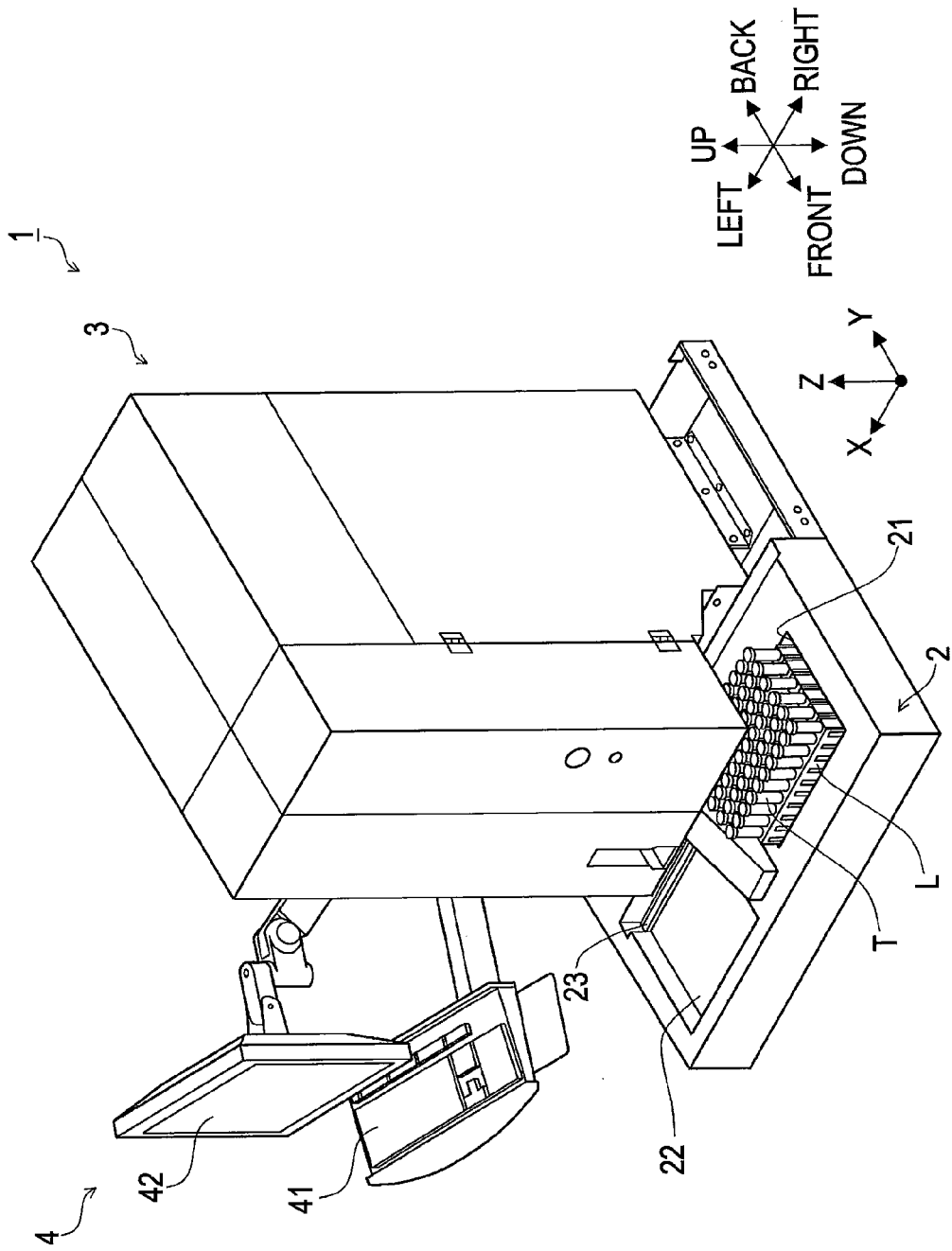

FIG. 8A

| CHANNEL | MEASUREMENT OBJECT | DETECTION SECTION | REAGENT |
|---|---|---|---|
| CBC | WBC (WHITE BLOOD CELLS) | OPTICAL TYPE FLOW CYTOMETRY | WBC STAINING AGENT AND HEMOLYTIC AGENT |
| | RBC (RED BLOOD CELLS) | SHEATH FLOW DC DETECTION | DILUTING LIQUID |
| | PLT (PLATELETS) | | DILUTING LIQUID |
| | HGB (HEMOGLOBIN) | SLS HEMOGLOBIN METHOD | HGB HEMOLYTIC AGENT |
| DIFF | WBC (WHITE BLOOD CELLS) | OPTICAL TYPE FLOW CYTOMETRY | DIFF STAINING AGENT AND HEMOLYTIC AGENT |
| | NEUT (NEUTROPHILS) | | DIFF STAINING AGENT AND HEMOLYTIC AGENT |
| | LYMPH (LYMPHOCYTES) | | DIFF STAINING AGENT AND HEMOLYTIC AGENT |
| | EO (EOSINOPHILS) | | DIFF STAINING AGENT AND HEMOLYTIC AGENT |
| | BASO (BASOPHILS) | | DIFF STAINING AGENT AND HEMOLYTIC AGENT |
| | MONO (MONOCYTES) | | DIFF STAINING AGENT AND HEMOLYTIC AGENT |
| RET | RET (RETICULOCYTES) | OPTICAL TYPE FLOW CYTOMETRY | RET STAINING AGENT AND HEMOLYTIC AGENT |
| PLT-F | PLT (PLATELETS) | OPTICAL TYPE FLOW CYTOMETRY | PLT STAINING AGENT AND HEMOLYTIC AGENT |
| WPC | Abnormal Lymph (ABNORMAL LYMPHOCYTES) | OPTICAL TYPE FLOW CYTOMETRY | WPC STAINING AGENT AND HEMOLYTIC AGENT |
| | Blast (BLASTOCYTES) | | |

FIG. 8B

| | COMBINED MEASUREMENT ITEMS |
|---|---|
| 1 | CBC |
| 2 | CBC, DIFF |
| 3 | CBC, DIFF, RET |
| 4 | CBC, DIFF, RET, PLT-F |
| 5 | CBC, DIFF, RET, PLT-F, WPC |
| ...... | ...... |

FIG. 9A

WORK LIST (PRE REVISION)

| HOLDER POSITION | SAMPLE ID | PATENT ID | MEASUREMENT ITEM (CHANNEL) | MEASUREMENT STATUS | RECORDING DATE/TIME |
|---|---|---|---|---|---|
| 1 | **** | **** | CBC, DIFF | UNMEASURED | : : |
| 2 | **** | **** | CBC | UNMEASURED | : : |
| 3 | **** | **** | CBC, DIFF | UNMEASURED | : : |
| 4 | **** | **** | CBC, DIFF | UNMEASURED | : : |
| 5 | **** | **** | CBC, DIFF | UNMEASURED | : : |
| 6 | **** | **** | CBC, DIFF, RET | UNMEASURED | : : |
| 7 | **** | **** | CBC | UNMEASURED | : : |
| 8 | **** | **** | CBC, DIFF | UNMEASURED | : : |
| 9 | **** | **** | CBC, DIFF, RET | UNMEASURED | : : |
| 10 | **** | **** | CBC, DIFF | UNMEASURED | : : |

FIG. 9B

WORK LIST (POST REVISION)

| HOLDER POSITION | SAMPLE ID | PATENT ID | MEASUREMENT ITEM (CHANNEL) | MEASUREMENT STATUS | RECORDING DATE/TIME |
|---|---|---|---|---|---|
| 1 | **** | **** | CBC, DIFF | UNMEASURED | : : |
| 2 | **** | **** | CBC, DIFF, RET | UNMEASURED | : : |
| 3 | **** | **** | CBC, DIFF | UNMEASURED | : : |
| 4 | **** | **** | CBC, DIFF | UNMEASURED | : : |
| 5 | **** | **** | CBC, DIFF | UNMEASURED | : : |
| 6 | **** | **** | CBC, DIFF, RET, PLT-F | UNMEASURED | : : |
| 7 | **** | **** | CBC | UNMEASURED | : : |
| 8 | **** | **** | CBC, DIFF | UNMEASURED | : : |
| 9 | **** | **** | CBC, DIFF, RET, PLT-F, WPC | UNMEASURED | : : |
| 10 | **** | **** | CBC, DIFF | UNMEASURED | : : |

FIG. 10A

MEASUREMENT RESULTS DATABASE

| SEQUENCE No. | PATIENT ID | SAMPLE ID | DATE OF MEASUREMENT | TIME OF MEASUREMENT | MEASUREMENT ITEMS | RE-EXAMINATION FLAG | MEASUREMENT DATA |
|---|---|---|---|---|---|---|---|
| ... | AAA | **** | 2011/11/22 | 15:16:20 | CBC, DIFF, RET | 1 | ... |
| ... | AAA | **** | 2011/11/22 | 10:21:48 | CBC, DIFF | 0 | ... |
| ... | BBB | **** | 2011/11/22 | 11:58:36 | CBC | 0 | ... |
| ... | CCC | **** | 2011/11/1 | 14:21:48 | CBC, DIFF | 0 | ... |
| ... | DDD | **** | 2011/12/18 | 10:15:01 | CBC, DIFF | 0 | ... |
| ... | DDD | **** | 2011/11/16 | 16:01:21 | CBC | 0 | ... |
| ... | EEE | **** | 2011/11/18 | 10:02:23 | CBC, DIFF | 0 | ... |
| ... | ... | ... | ... | ... | ... | ... | ... |

FIG. 10B

<MEASUREMENT ITEM RESET>

C1 ☐ RESET
  C2 ☐ SELECT MANY MEASUREMENT ITEMS
  C3 ☐ USE SIMULATION RESULTS
  C4 ☐ USE MOST RECENT RE-EXAMINATION MEASUREMENT RESULTS
    C5 ☐ SET MEASUREMENT PERIOD: ____ R1 DAYS PRIOR
  C6 ☐ REFERENCE MOST RECENT MEASUREMENT RESULTS
  C7 ☐ REFERENCE MOST RECENT RE-EXAMINATION MEASUREMENT RESULTS
    C8 ☐ SET MEASUREMENT PERIOD: ____ R2 DAYS PRIOR

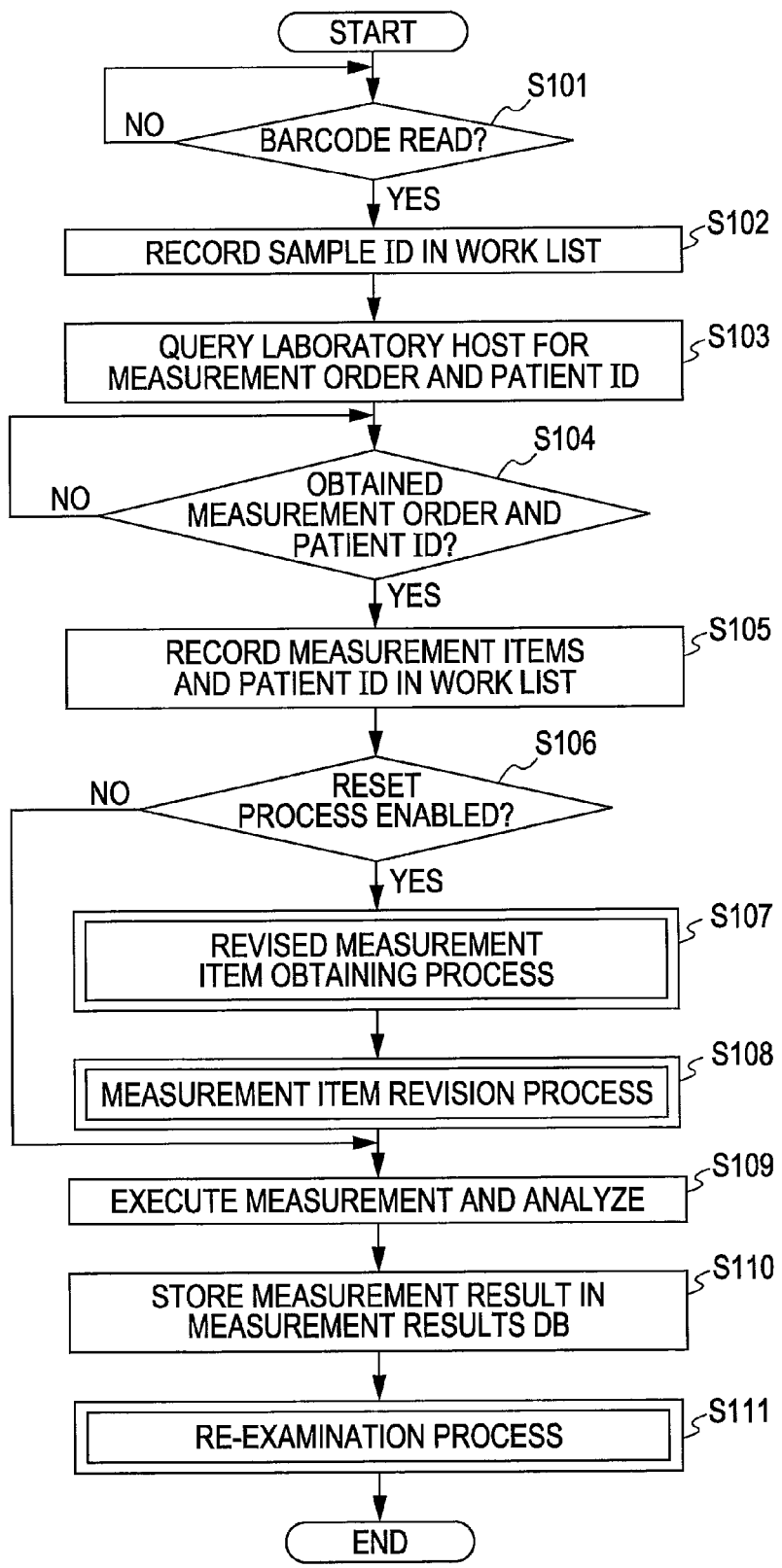

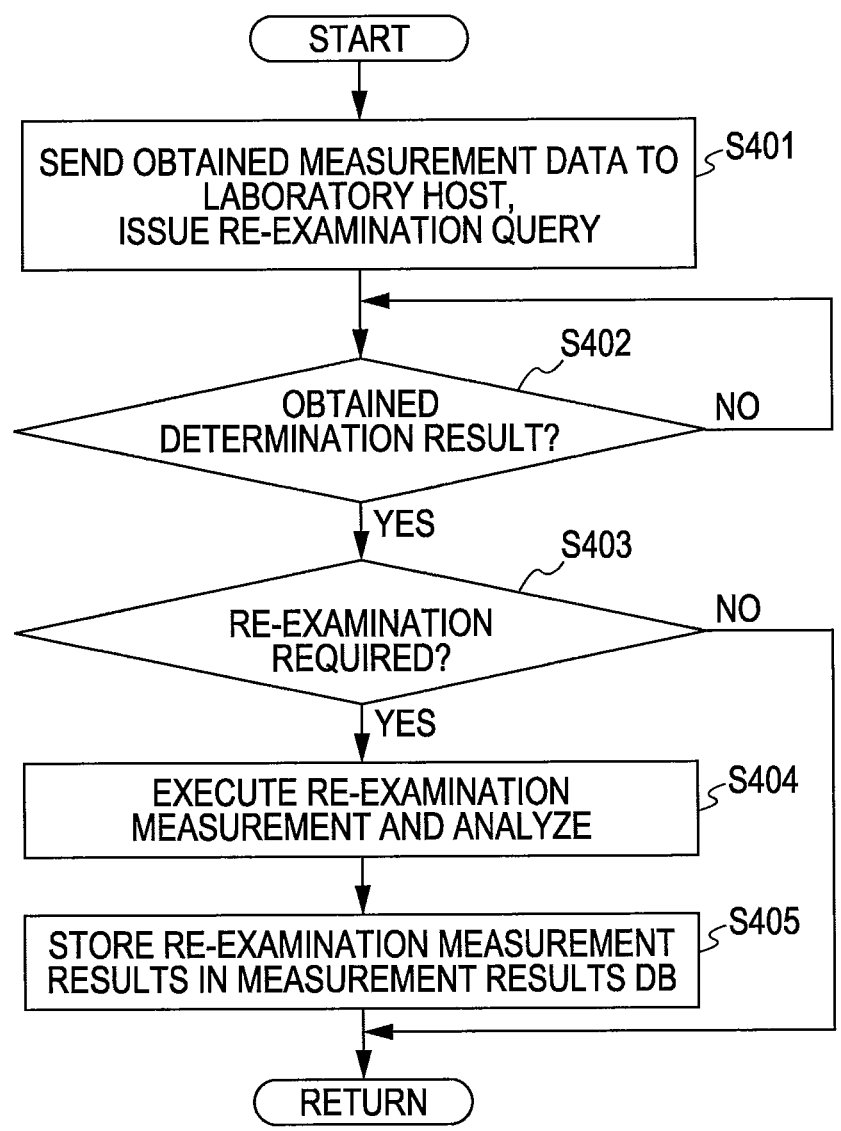

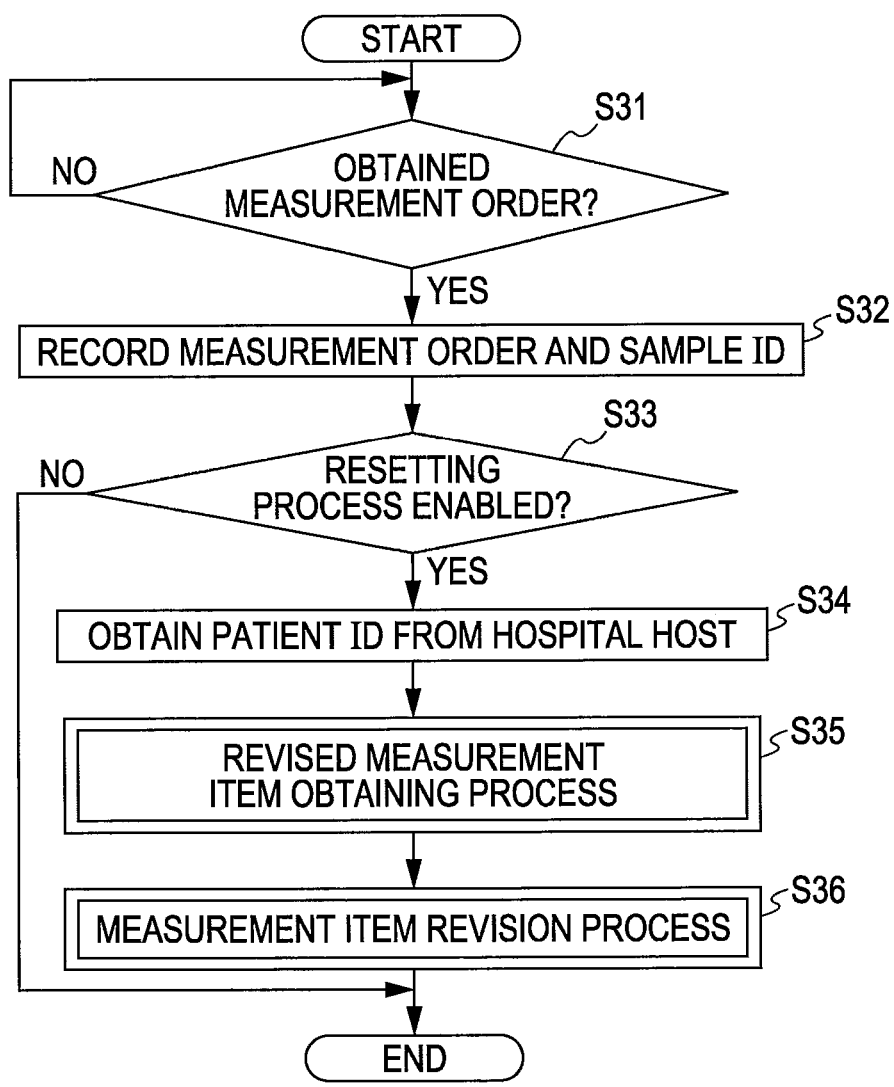

SAMPLE ANALYZER, SAMPLE ANALYZING METHOD, AND SAMPLE ANALYZING SYSTEM

RELATED APPLICATIONS

This application claims priority under 35 U.S.C. §119 to Japanese Patent Application No. 2012-080322 filed on Mar. 30, 2012, the entire content of which is hereby incorporated by reference.

BACKGROUND OF THE INVENTION

1. Field of the Invention

The present invention relates to a sample analyzer, sample analyzing method, and sample analyzing system for measuring and analyzing samples such as blood for specific measurement items.

2. Description of the Related Art

When measuring a sample using a sample analyzer, measurement results are obtained for the purposes of diagnosis and treatment by performing a second measurement (re-examination) according to the result of a first measurement (initial examination) of any given sample. On the other hand, it is desirable to effectively limit the number of re-examinations from the perspective of reducing the examination time and cost.

Japanese Laid-Open Patent Publication No. 5-119042 discloses a method of calculating an estimation value based on a previous measurement value of the same patient, and adjusting the sample dispensing amount or the sample dilution ratio based on the calculated estimation value. According to this method, preprocessing of a sample is rationalized to reduce the number of re-measurements.

Examination of samples frequently may include sample analysis performed on different days for the same patient. In this case, more appropriate analysis can be performed when the measurement results of prior examinations are reflected in the measurement items of the current analysis.

For example, when it is determined that re-examination is required for a previous analysis in which the examination has been performed for more detailed measurement items, the current analysis will often include examination at least the same detailed measurement items as previously. When the basis of the determination for re-examination has been modified, re-examination may not be necessary in the current measurements according to the modified determination basis; however, there may be times when examination of more detailed measurement items are required as a result of applying the current measurement results to the current determination basis. In this case, measurement of these more detailed measurement items are often performed in the current measurement.

In this case, more appropriate analysis can be performed when the measurement results of prior examinations are reflected in the measurement items of the current analysis. Japanese Laid-Open Patent Publication No. 5-119042 only discloses a method for adjusting the sample dispensing amount and sample dilution ratio based on the previous measurement results, and does not in any way mention modification of the measurement items.

SUMMARY OF THE INVENTION

The scope of the present invention is defined solely by the appended claims, and is not affected to any degree by the statements within this summary.

An object of the present invention is to provide a sample analyzer, sample analyzing method, and sample analyzing system optimizing analysis with high efficiency by suiting the measurement items of a sample to the patient.

A first aspect of the present invention is a sample analyzer comprising:

a measurement section capable of measuring a sample contained in a sample container on a plurality of measurement items;

an information obtaining section for obtaining identification information of the sample contained in the sample container; and a controller configured for performing operations, comprising:

obtaining a measurement order which has been set for the identification information of the sample, based on the identification information of the sample obtained by the information obtaining section;

obtaining historical measurement information which is based on past measurement histories of a subject from whom the sample corresponding to the identification information of the sample was collected; and setting measurement items for the sample based on the obtained measurement order and the obtained historical measurement information.

A second aspect of the present invention is a sample analyzing method for measuring and analyzing a sample for predetermined measurement items, the method comprising:

obtaining identification information of the sample contained in the sample container;

obtaining a measurement order which has been set for the identification information of the sample, based on the obtained identification information of the sample;

obtaining historical measurement information which is based on past measurement histories of a subject from whom the sample corresponding to the identification information of the sample was collected; and setting measurement items for the sample based on the obtained measurement order and the obtained historical measurement information.

A third aspect of the present invention is a sample analysis system for measuring and analyzing a sample for a plurality of types of measurement items, the system comprising:

a sample analyzer for measuring and analyzing a sample for predetermined measurement items; and a host computer capable of communicating with the sample analyzer, wherein the host computer comprises a controller configured for performing operations, comprising:

setting measurement items for a sample based on the historical measurement information which is based on past measurement histories of the subject corresponding to the sample, and a measurement order set for the sample; and a transmission section for transmitting the set measurement items to the sample analyzer.

As stated above, the present invention provides a sample analyzer, sample analyzing method, and sample analyzing system that optimizes analysis with high efficiency by suiting the measurement items of a sample to the patient.

BRIEF DESCRIPTION OF THE DRAWINGS

FIG. 1 briefly shows the network system of the embodiment;

FIG. 2 is a perspective view showing an external view of an embodiment of the sample analyzer;

FIGS. 8A and 8B illustrate the combinations of the measurement item content in the embodiment;

FIGS. 9A and 9B show the structures of the work lists of the embodiment;

FIGS. 10A and 10B show the measurement item database and the setting screen for resetting the rules of the measurement items in the embodiment;

FIGS. 11A and 11B are flow charts showing the measurement item setting processes of the embodiment;

FIG. 15 is a flow chart showing the re-examination process of the embodiment;

FIGS. 17A-17C are flow charts showing the measurement item setting process, measurement order transmission process, and measurement result storage process in the laboratory host of the first modification.

DETAILED DESCRIPTION OF THE PREFERRED EMBODIMENTS

Figure 3B:
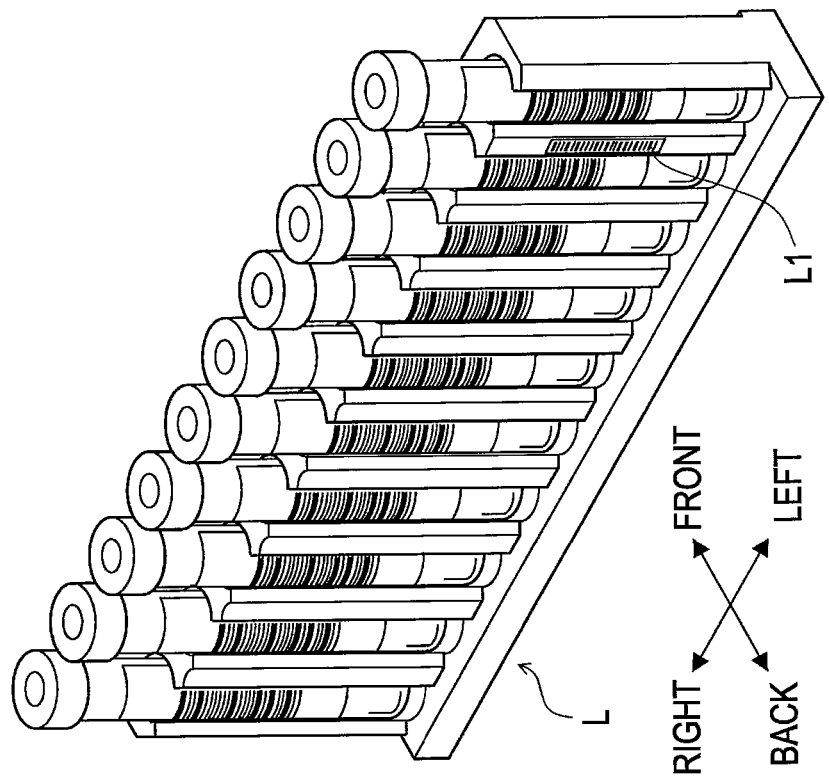
FIGS. 3A and 3B show the structures of the rack and sample container of the embodiment.

The preferred embodiments of the present invention will be described hereinafter with reference to the drawings.

The present embodiment applies the invention to an examination system for performing examinations and analysis of blood. The sample analyzer of the embodiment is described below referring to the drawings.

FIG. 1 shows a structural example of the examination system of the embodiment.

The examination system of the present embodiment shown in FIG. 1 is configured by a sample analyzer 1 and host computer (hereinafter referred to as "laboratory host") 10 installed in a laboratory, host computer (hereinafter referred to as "examination room host") 20 installed in the examination room, host computer (hereinafter referred to as "collection room host") 30 installed in a blood collection room, and host computer (hereinafter referred to as "hospital host") 40 for consolidating and managing information related to examinations. The laboratory host 10, examination room host 20, collection room host 30, and hospital host 40 are mutually connected to be capable of intercommunications. The laboratory host 10 and the sample analyzer 1 also are mutually connected to be capable of intercommunications.

The sample analyzer 1 is a blood cell counter for detecting and counting various blood cells including white blood cells, red blood cells and platelets in blood samples. The sample analyzer 1 has a plurality of detection units for performing different detection processes to detect each type of blood cell, which will be described later. The sample analyzer 1 selects the detection unit according to the measurement order obtained from the laboratory host 10, and measures the sample via the selected detection unit.

In this examination system the measurement data are, for example, input to the examination host 20 by the physician. In this case the patient ID provided to each patient is also entered. The input measurement data are transmitted together with the patient ID from the examination room host 20 to the hospital host 40, and stored in a database on the hospital host 40. Thereafter, blood (sample) is drawn from the patient in the collection room, and a barcode label that includes the sample ID is adhered to the sample container that contains the drawn sample. The sample ID is transmitted together with the date and time of the collection from the collection room host 30 to the hospital host 40 and stored on the hospital host 40 so as to be associated with the patient ID and the sample measurement data. Then, the recorded measurement data and sample ID are transmitted from the hospital host 40 to the laboratory host 10 and stored in a database on the laboratory host 10.

The sample analyzer 1 measures the predetermined measurement items on the sample brought from the collection room. The sample analyzer 1 obtains a measurement order for the sample from the laboratory host 10 in these measurements. In addition to the measurement order obtained from the laboratory host 10 in the present embodiment, past measurement results of the patient (subject) from whom the sample was collected are referenced, and the measurement items for the sample are set based on the measurement order and the past measurement results.

In the present embodiment, measurement items standardize the content of the measurements by combining the measurement object, detection unit used for the measurement, and reagent. Even when the measurement object is the same, the measurement items are different if the combination of reagent and detection unit used for the measurement are different. For example, the measurement items will differ depending on whether the detection unit is an electrical resistance type or optical type even though the measurement object is platelets in both cases.

FIG. 2 is an exterior perspective view of a sample analyzer 1. The sample analyzer 1 is configured by a transport unit 2, measurement unit 3, and information processing unit 4.

The transporting unit 2 is disposed in front of the measurement unit 3, and is configured by a right table 21, left table 22, and a rack transporter 23 connecting the right table 21 and the left table 22. The right table 21 and the left table 22 can accommodate a plurality of racks L that are capable of holding ten sample containers T.

In the transporting unit 2, the right table 21 accommodates racks L placed in the right table 21 by the user. The transporting unit 2 transports the rack L held on the right table 21 to a predetermined position of the rack transporter 23 to supply the sample containers T to the measurement unit 3. The transporting unit 2 then transports the rack L on the rack transporter 23 to the left table 22. The containers in the rack L are picked up for processing by the measurement unit 3 at the take-up position P3 (refer to FIG. 4) on the rack transporter 23.

Figure 3A:
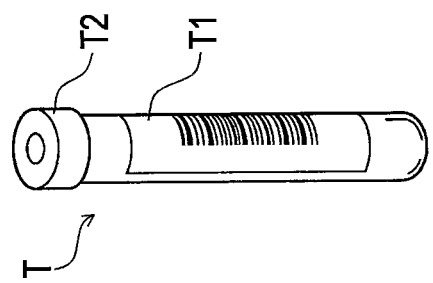

FIGS. 3(a) and (b) are respectively perspective views showing the structures of the sample container T and the rack L.

Referring to FIG. 3(a), the sample container T is a tube-like container, open at the top end, formed of transparent synthetic resin or glass. A barcode label T1 is adhered to the side surface of the sample container T. A barcode including the sample ID is printed on the barcode label T1. The sample container T contains a blood sample of whole blood collected from a patient, and the opening at the top end is sealed with a rubber cap T2.

Referring to FIG. 3(b), a barcode label L1 is adhered to the back side of the rack L. A barcode indicating the rack ID is printed on the barcode label L1. The rack L has holders capable of vertically holding ten sample containers T.

Returning to FIG. 2, the measurement unit 3 picks up the sample container T from the rack L via a hand part 31 (refer to FIG. 4) at the take-up position P3 (refer to FIG. 4) of the rack transporter 23, and moves the sample container T into the measurement unit 3. Then the sample contained in the sample container T is measured inside the measurement unit 3. When the measurement is completed, the measurement unit 3 returns the sample container T back to the original holder of the sample rack L.

The information processing unit 4 has an input part 41 and a display part 42. The information processing unit 4 also is connected to the transporting unit 2 and the measurement unit 3 so as to be capable of intercommunication. The information processing unit 4 controls the operation of the transporting unit 2, the measurement unit 3, and performs analysis based on the measurement results of the measurement units 3.

Figure 4:
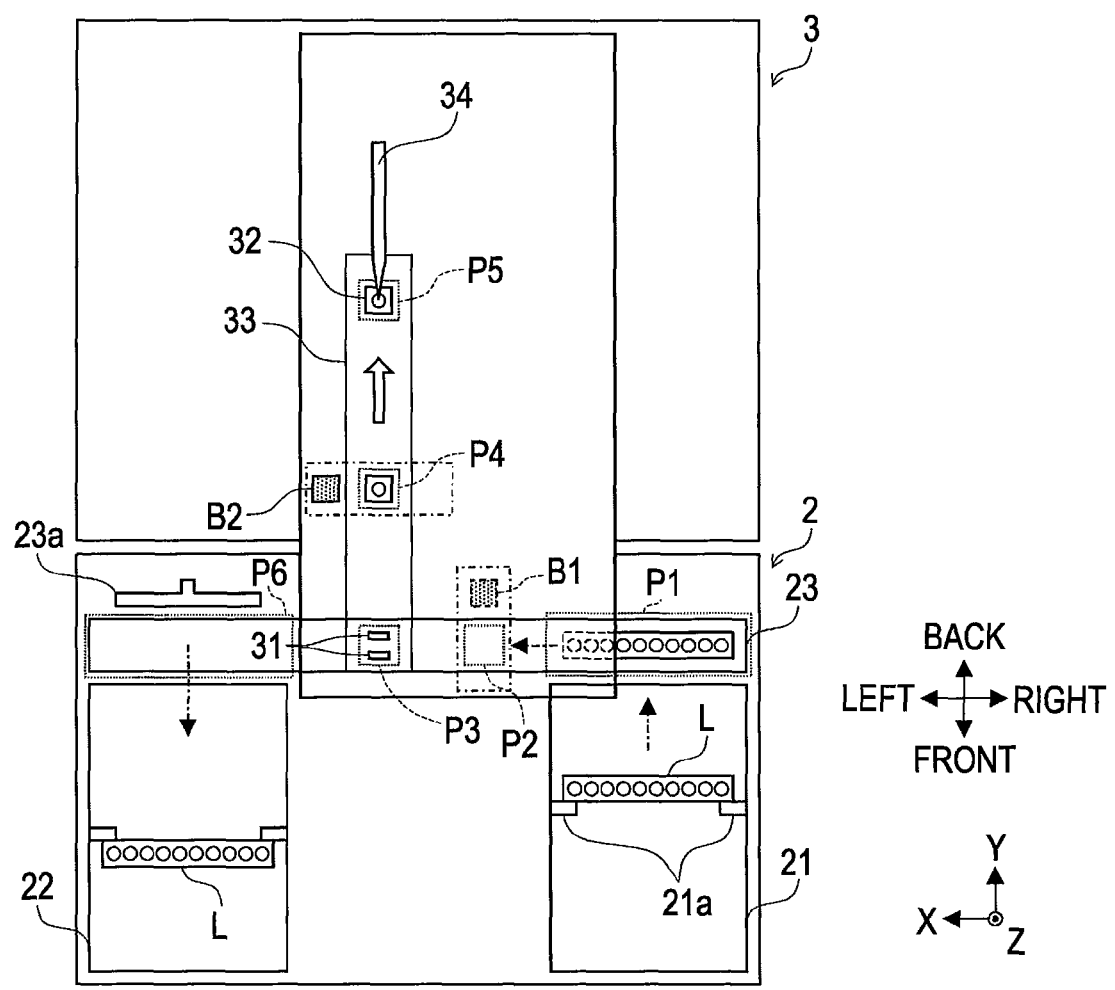
FIG. 4 is a schematic view showing the structures of the transporting unit and measurement unit of the embodiment viewed from above.

FIG. 4 schematically shows the structures of the transporting unit 2 and the measurement unit 3 viewed from above.

The rack L loaded in the right table 21 is moved to the feed position P1 on the right end of the rack transporter 23 by the rack mover 21a. The rack L is moved to the left by a belt (not shown in the drawing) of the rack transporter 23. When the holder of the rack L is thereafter disposed at the barcode reading position P2 in front of the barcode reader B 1, a predetermined detection unit determines whether a sample container T is held in the holder. When a sample container T is held in the holder, the barcode reader B1 reads the sample ID from the barcode label T1 of the sample container T. When the barcode label L1 of the rack L is disposed in front of the barcode reader B1, the barcode reader B1 reads the rack ID from the barcode label L1 of the rack L.

When the barcode information is read, the sample container T is disposed at the take-up position P3 of the measurement unit 3. The hand part 31 is provided in the measurement unit 3 so as to be movable in vertical directions (Z-axis direction) at the take-up position P3. When the sample container T is disposed at the take-up position P3, the sample container T is gripped by the hand part 31 and moved in the upward direction (positive Z-axis direction) The hand part 31 moves the sample container T in a pendulum-like fashion to mix the sample. At this time the container placement part 32 is moved above the take-up position P3. When mixing is completed, the hand part 31 moves in a downward direction (negative Z-axis direction) and the container held by the hand part 31 is set in the container placement part 32.

The sample placement part 32 is thereafter moved to the barcode reading position P4 by the container transporter 33, and the barcode reader B2 reads the barcode to verify the sample container T. The sample container T then is moved to the aspirating position P5 in conjunction with the movement of the container placement part 32. When the When the container placement part 32 is disposed at the aspirating position P5 directly below piercer 34, the piercer 34 moves downward to aspirate the sample from the sample container T disposed at the aspirating position P5.

When the aspiration of the sample by the piercer 34 ends, the container placement part 32 is moved forward and set again at the take-up position P3. At the take-up position P3, the container T is picked up from the container placement part 32 in an upward direction by the hand part 31. In this state, the container placement part 32 is moved backward. The hand part 31 is then moved downward (negative Z-axis direction), and the sample container T is returned to the original holder of the rack L disposed on the rack transporter 23. Thereafter, the sample container T of the next holder of the rack L is supplied to the measurement unit 3. When all sample containers T of the rack L have been measured, the rack L is disposed at the collection position P6. The rack L is then discharged to the left table 22 by the rack pusher 23a.

Figure 5:
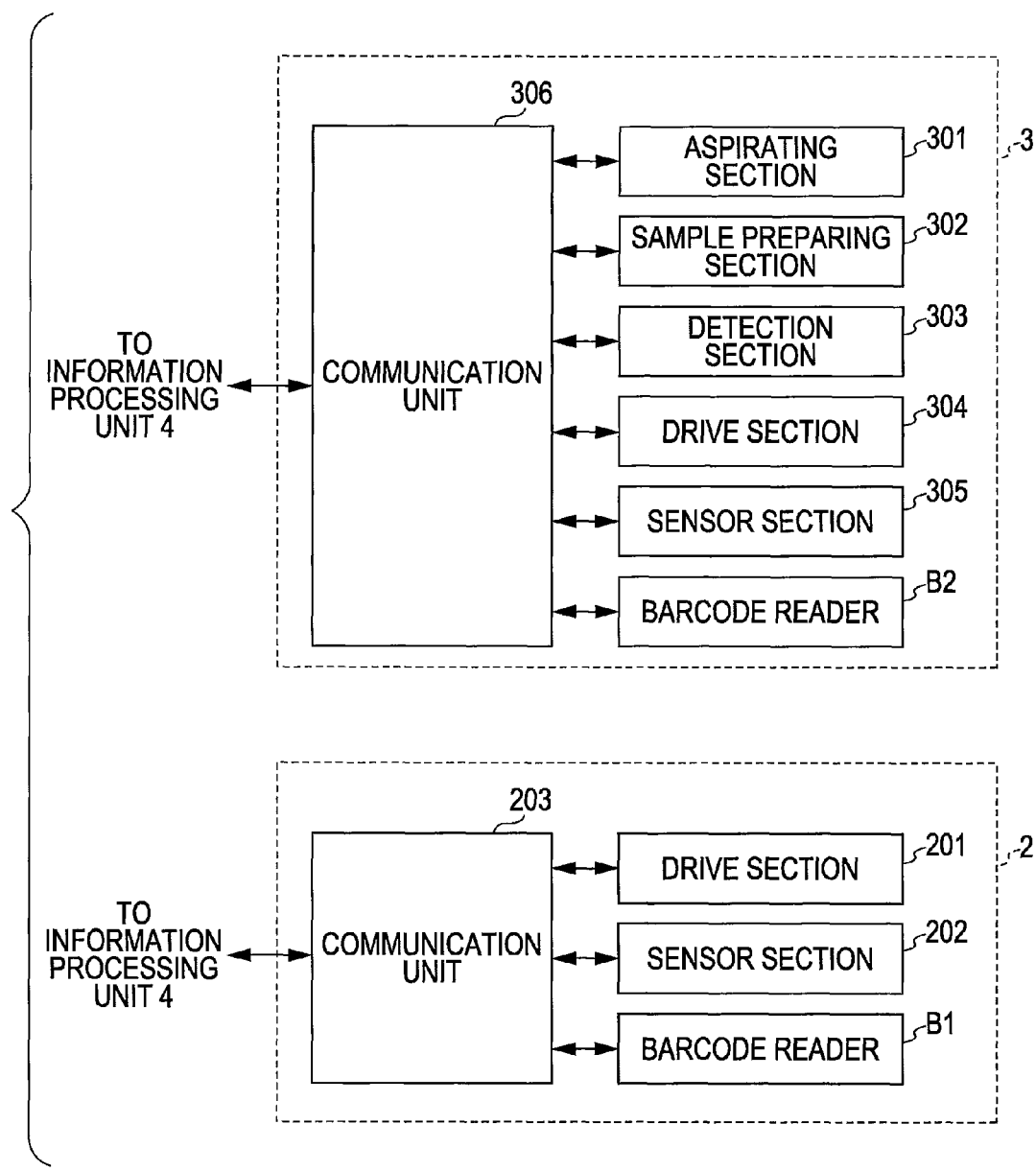
FIG. 5 briefly shows the structures of the transporting unit and the measurement unit of the embodiment.

FIG. 5 briefly shows the structures of the transporting unit 2 and the measurement unit 3.

The transporting unit 2 has a drive section 201, sensor section 202, barcode reader B1, and communication unit 203.

The drive section 201 includes a device for transporting the rack L within the transporting unit 2. The sensor section 202 includes sensors for detecting the rack L at predetermined positions on the transport path of the transporting unit 2. The barcode reader B1 reads the barcode labels adhered to the rack L and the sample container T, respectively. The communication unit 203 is connected to the information processing unit 4 and is capable of communication therewith. Each section in the transporting unit 2 is controlled by the information processing unit 4 through the communication unit 203. Signals output from the various sections in the transporting unit 2 are also transmitted to the information processing unit 4 through the communication unit 203.

The measurement unit 3 has an aspirating section 301, sample preparing section 302, detecting section 303, drive section 304, sensor section 305, barcode unit B2, and communication unit 306.

Figure 6:
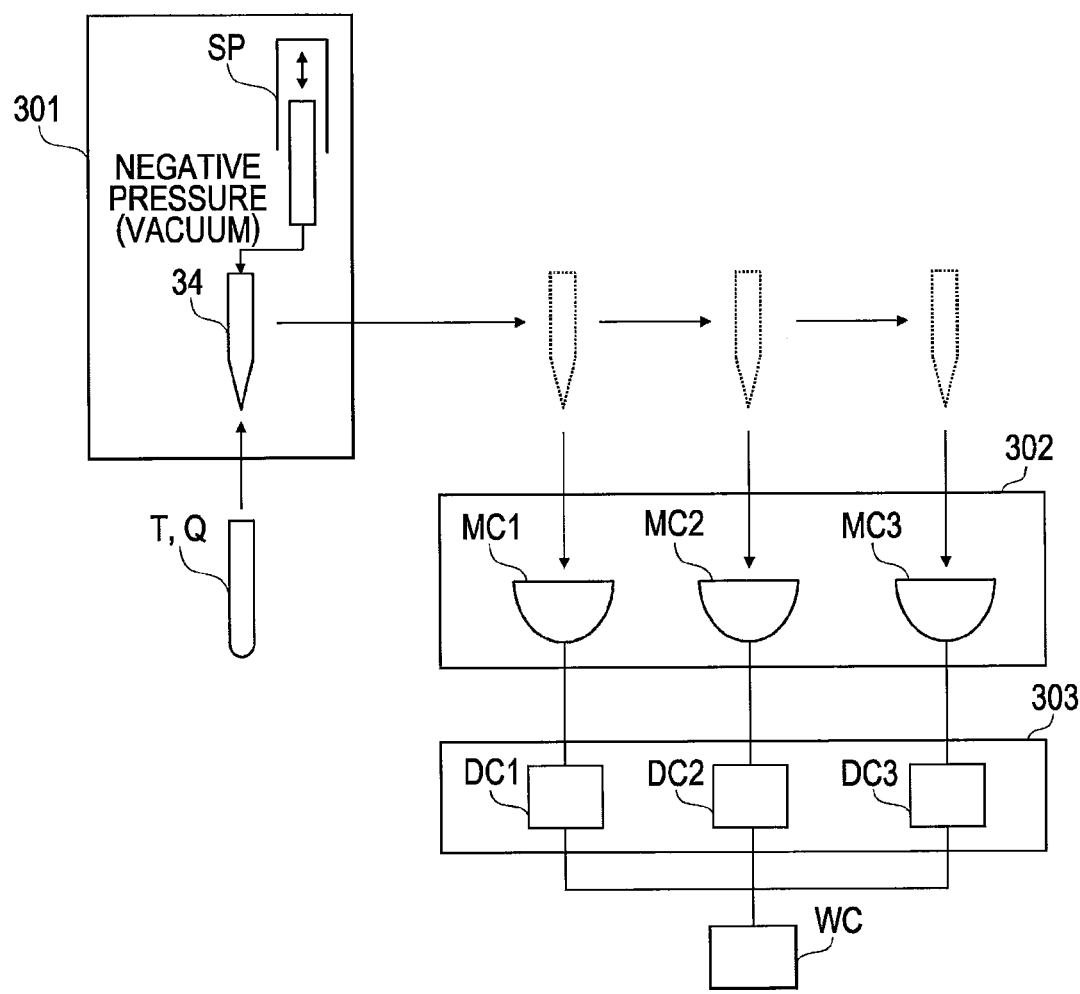
FIG. 6 briefly shows the structure of the fluid circuit of the measurement unit of the embodiment.

FIG. 6 briefly shows the fluid circuit of the measurement unit 31.

The aspirating section 301 includes the piercer 34 for aspirating the sample contained in the sample container T that is transported within the measurement unit 3, and a syringe pump SP for producing a negative pressure to the piercer. The sample preparing section 302 is provided with reaction chambers MC1, MC2, and MC3 for mixing and agitating the sample and reagents. Note that although only a single reaction chamber MC2 is shown in FIG. 6, four reaction chambers MC2 are actually provided, and one reaction chamber MC2 is used in accordance with the reagent mixed with the sample.

The detecting section 303 is provided with an electrical resistance type detector DC1 (detector based on the sheath flow DC detection method) for detecting red blood cells and platelets, an optical detector DC2 (detector based on optical type flow cytometry) for detecting white blood cells and neutrophils, and an optical type detector DC3 (detector based on SLS hemoglobin method) for detecting hemoglobin. Samples prepared by the reaction chambers MC1 through MC3 are moved to the detectors DC1 through DC3, respectively. The measurement unit 3 also has a waste fluid chamber WC for storing waste fluids.

The electrical resistance type detector DC1 detects the change in the electrical signal as the characteristics amount of blood cell when a voltage is applied to a sample flowing through a flow cytometer. The optical type detector DC2 detects the amount of scattered light and the amount of fluorescent light received as the characteristic amount of blood cells when a laser light irradiates a sample flowing through a flow cytometer. The optical type detector DC3 detects the amount of light (absorbance) as the characteristic amount of blood cells when light from an LED irradiates a sample discharged to the measurement container.

When measuring a sample, the aspiration section 301 aspirates the sample through the piercer 34 by inducing a negative pressure in the piercer 34 via the syringe pump SP, and discharges the sample to the reaction chambers MC1, MC2, MC3. The sample preparing section 302 also stirs and mixes the samples and reagent within the reaction chambers MC1, MC2, and MC3 to prepare a sample for measuring. The sample prepared in the reaction chamber MC 1 is moved to the electrical resistance type detector DC1 through a flow path. The sample prepared in the reaction chamber MC2 is moved to the optical type detector DC2 through a flow path. The sample prepared in the reaction chamber MC3 is moved to the optical type detector DC3 through a flow path.

The detection section 303 obtains the electrical signals detected by the electrical resistance detector DC1 as sample data. The detection section 303 also obtains the signals (side scattered light signals, forward scattered light signals, side fluorescent light signals) detected by the optical type detector DC2 as sample data. The detection section 303 further obtains signals detected by the optical type detector DC3 as sample data. The samples that have passed through the detecting section 303 are then moved to the waste liquid chamber WC through a flow path.

Returning to FIG. 5, the drive section 304 includes a mechanism to transport the sample container T within the measurement unit 3. The sensor section 305 includes sensors to detect the sample container T at predetermined positions on the transport path within the measurement unit 3. The barcode reader B2 reads the barcode label adhered to the sample container T transported in the measurement unit 3.

Figure 7:
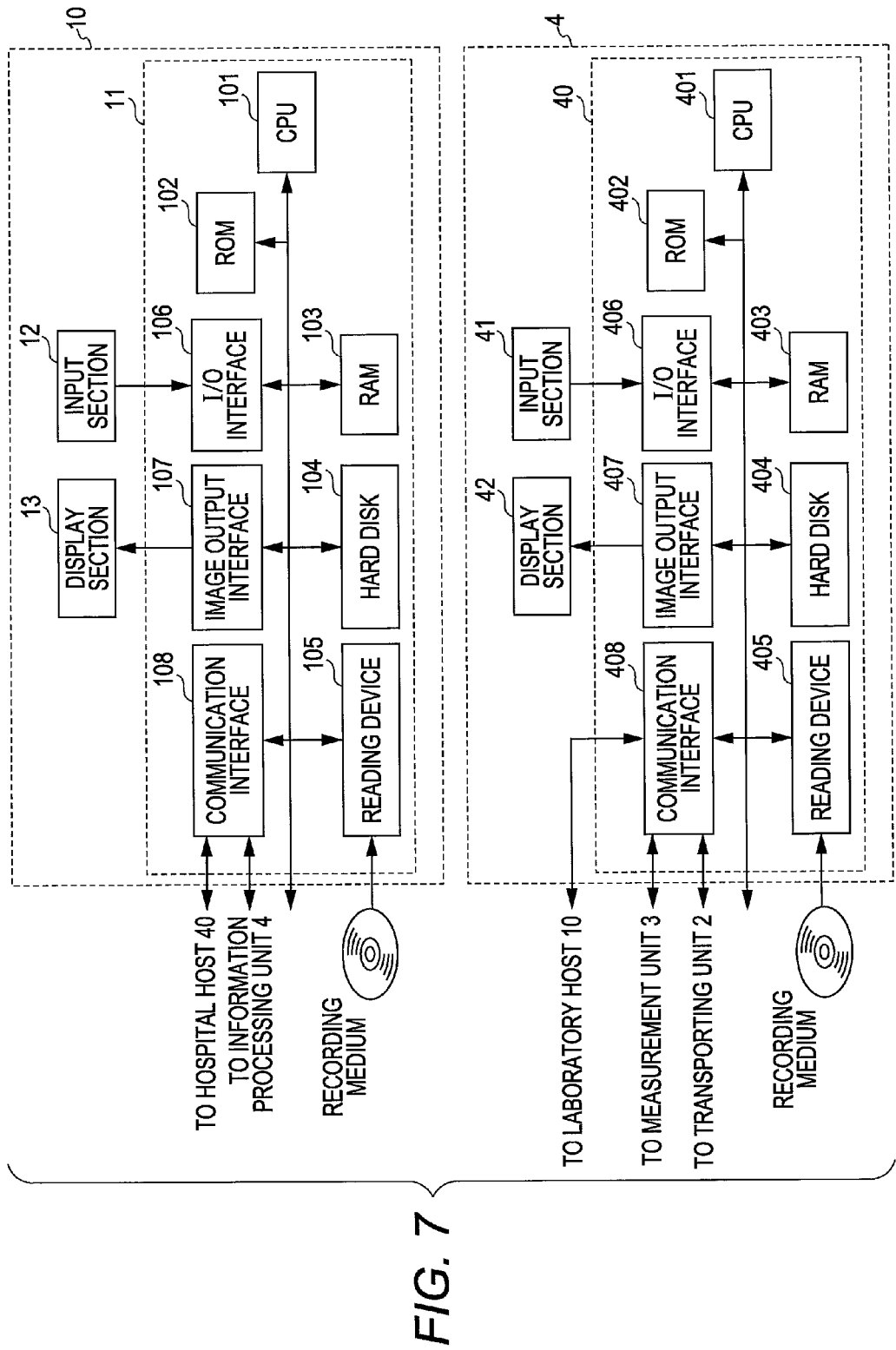
FIG. 7 briefly shows the structures of the laboratory host and the information processing unit of the embodiment.

FIG. 7 briefly shows the structures of the information processing unit 4 and the laboratory host 10.

The information processing unit 4 is configured by a personal computer having a main body 40, input section 41, and display section 42. The main body 40 has a CPU 401 ROM 402, RAM 403, hard disk 404, reading device 405, I/O interface 406, image output interface 407, and communication interface 408.

The CPU 401 is capable of executing a computer program stored in the ROM 402 and a computer program loaded in the RAM 403. The RAM 403 is used when reading the computer program stored in the ROM 402 and recorded on the hard disk 404. The RAM 403 is also used as the work area of the CPU 401 when the CPU 401 executes the computer programs.

An operating system and application programs, as well as the data used when executing the operating system and application programs that are executed by the CPU 401, are installed on the hard disk 404. That is, the hard disk 404 stores programs for analyzing the sample data transmitted from the measurement unit 3 and generating measurement results such as the red blood cell count and white blood cell count, and showing results on the display section 42 based on the generated measurement results.

Work list and measurement result database are also stored on the hard disk 404. The work list and the measurement result database are described later with reference to FIGS. 9 and 10. A program for setting the measurement items of each sample is also installed on the hard disk 404.

The reader 405 is a CD drive or DVD drive capable of reading computer programs and data recorded on a recording medium. The I/O interface 406 is connected to the input section 41 which includes a mouse and keyboard. The operator uses the input section 41 to enter data and instructions to the information processing unit 4. The image output interface 407 is connected to the display section 42 configured by a display of some type, and the image output interface 407 outputs image signals corresponding to the image data to the display 42.

The display section 42 displays images based on the input image signals. Various types of program screens are shown on the display section 42. The information processing unit 4 is capable of transmitting and receiving data to/from the transporting unit 2, measurement unit 3, and laboratory host 10 through the communication interface 408.

The laboratory host 10 is a personal computer having a main body 11, input section 12, and display section 13 similar to the information processing unit 4. The main body 11 has a CPU 101, ROM, 102, RAM 103, hard drive 104, reading device 105, I/O interface 106, image output interface 107, and communication interface 108 similar to the information processing unit 4.

Various computer programs that are executed by the CPU 401, and data used in the execution of these programs are installed on the hard disk 104. A database recording the measurement data received from the hospital host 40, and re-examination rules for determining whether re-examination is required based on the measurement results received from the information processing unit 4 and determining the re-examination measurement order also are stored on the hard disk 104. The laboratory host 10 also can transmit and receive data to/from the information processing unit 4 and hospital host 40 through the communication interface 108. The laboratory host 10 also can transmit and receive data to/from the examination room host 20 and the collection room host 30 through the communication interface 108.

FIG. 8(a) illustrates the measurement items that are settable in the sample analyzer 1. The measurement objects shown in FIG. 8(a) are representative in each channel, and other measurement objects also may be included.

FIG. 8(a) shows blood cells as the measurement object, the detection sections used to detect each blood cell, and the reagents used to detect each blood cell. When measuring the blood cell listed in the column "measurement object," the sample becomes a measurement sample by mixing with the reagent listed in the "reagent" column in the reaction chamber corresponding to the reagent being used. The prepared measurement sample is moved to the detection unit of the type listed in the "detection unit" column, and the blood cells are then measured. The sheath flow DC method, optical flow cytometry, and SLS hemoglobin method listed in the "detection unit" column respectively represent the electrical resistance type detection unit MC1, optical type detection unit MC2, and optical type detection unit MC3 of FIG. 6.

The measurement items can be selected and set in channel units. The CBC channels include WBC (white blood cells), RBC (red blood cells), PLT (platelets), and HGB (hemoglobin) as measurement object blood cell types. Samples are mixed with diluting liquid for measurements performed by the electrical resistance type detection unit MC1 when measuring RBC and PLT. Samples are mixed with HGB hemolytic agent for measurement performed by the optical type detection unit MC3 when measuring HGB. Samples are mixed with WBC staining agent and hemolytic agent for measurement performed by the optical type detection unit MC2 when measuring WBC.

The DIFF channels include WBC (white blood cells), NEUT (neutrophils), LYMPH (lymphocytes), EO (eosinophils), BAS (basophils), MONO (monocytes) as measurement object blood cells. A sample is mixed with a DIFF staining agent and hemolytic agent for measurement by the optical type detection unit MC2 in the measurement of each of the above types of blood cells. The RET channel includes only RET (reticulocytes) as the measurement object. A sample is mixed with a RET staining agent and diluting liquid for measurement by the optical type detection unit MC2 in the RET measurement. The PLT channel includes PLT as the measurement object. Unlike the CBC channel, the PLT channel uses the optical type detection unit MC2 to measure a sample mixed with PLT staining agent and diluting liquid.

In the WPC channel, the blood cells are not counted; flags indicating the appearance of abnormal lymphocytes and blastocytes are obtained from the state of the cell distribution in a scattergram having the forward scattered light intensity and side fluorescent light intensity as coordinate axes. Although these flags are also obtainable in the measurements of the DIFF channel, the accuracy of the flags is increased in the WPC channel by using a stained sample that is different from the stained sample used in the DIFF channel. A sample is mixed with a WPC staining agent and hemolytic agent for measurement by the optical type detection unit MC2 in the measurement of the WPC channel.

As described above, the measurement items standardize the content of the measurements by combining the measurement object, detection unit used for the measurement, and reagent. In the case shown in FIG. 8, the combination of the blood cells listed in each column of "measurement object," the reagent and the detection unit used for the measurement of each type of blood cell compose the measurement items. Therefore, although the PLT of the CBC channel and the PLT of the PLT-F channel are the same measurement object blood cells, they are mutually different measurement items because the reagent and detection units used for the measurements are mutually different. Similarly, the WBC of the CBC channel and the WBC of the DIFF channel are also mutually different measurement items because the reagents used in the measurements are different.

The reaction chamber MC1 of FIG. 6 is used to measure RBC and PLT of the CBC channel. The reaction chamber MC3 is used to measure HGB of the CBC channel. One reaction chamber among the four reaction chambers MC2 is used to measure WBC of the CBC channel, one is used to measure blood cells of the DIFF channel, one is used for measurements of the WBC channel, and the remaining reaction chamber is used for measurements of the RET channel and the PLT-F channel. In the measurements of the RET channel and the PLT-F channel, the sample in the reaction chamber is discarded after the sample is mixed with PLT staining agent and diluting liquid in the reaction chamber MC2 and the measurements of the PLT-F channel have been performed. Subsequently, the sample is mixed with the RET staining agent and the diluting liquid in the same reaction chamber MC2, and the measurements of the RET channel are performed.

FIG. 8(b) shows the method of combining the measurement items.

As described above, the measurement items can be selected and set in channel units. Selection of the CBC channel is mandatory and the measurement items of the CBC channel are invariably selected. That is, the measurement items of the CBC channel required basic items, and measurement items are selected by setting the measurement items of the CBC channel alone or in combination with the other channels. Channels other than the CBC channel cannot be selected or set independently, although one or a plurality of channels may be optionally selected in addition to the CBC channel.

FIG. 9(a) shows the structure of the work list stored in the information processing unit 4.

Referring to FIG. 9(a), the work list associates the sample holding position on the rack L, the sample ID of the sample held at each holding position, the patient ID of the patient from whom each blood sample was collected, the measurement items corresponding to the sample held at each holding position, the measurement status of each sample, and the date and time when the measurement item was recorded in the work list. Since the measurement items are selectable in channel units, the channel is recorded in the measurement items of FIG. 9(a). A work list is prepared for each rack L, and generated by reading the sample ID from the barcode label T1 of each sample container T via the barcode reader B1 of FIG. 4. The work list may also include items other than the items shown in FIG. 9(a). The recording sequence of the data in the work list will be described later with reference to FIG. 11.

FIG. 10(a) shows the structure of the measurement result database stored in the information processing unit 4.

Referring to FIG. 10(a), the measurement result database is a list associating the patient ID, sample ID, measurement date, measurement time, measurement items, re-examination flag, and measurement data for each sequence number. The measurement result database may also include items other than the items shown in FIG. 10(a).

When the measurement of a single sample is completed in the measurement unit 3, one line of data is added to the measurement result database. That is, when measurement of a single sample is completed, the sequence number is incremented by [1] and a single line of storage area is prepared. The patient ID of the patient from whom the sample was collected, the sample ID of the sample, the date and time of the measurement of the sample, the measurement items of the sample, and the measurement data obtained by the measurement of the sample are stored in this area of the database. A [1] is stored in the area of the re-examination flag when the measurement of the sample is a measurement obtained by re-examination, and a [0] is stored in the area of the re-examination flag when the measurement was not obtained by re-examination.

When new measurement results are obtained and the measurement results database has reached the maximum capacity for storing sample data, the oldest measurement results are deleted to provide a storage area for the new measurement results. The measurement results history is associated with the patient ID and stored in the measurement results database.

In the present embodiment the measurement items recorded by the attending physician and examining physician can be reset based on the past measurement results of the patient stored in the measurement results database in the information processing unit 4. The sample collected from the patient is subjected to measurements in accordance with the reset measurement items. The measurement item resetting process can be enabled by the user initially enabling the resetting process in the information processing unit 4 beforehand. The measurement item resetting method used in the resetting process is user selectable.

FIG. 10(b) shows the resetting screen for resetting the content of the measurement item resetting process. Note that symbol designations C1 through C8 represent the checkboxes at the upper left in FIG. 10(b). The symbol designations R1 and R2 entered in the input fields are symbols assigned for descriptive purposes and are not displayed on the screen. This screen is shown on the display section 42 of the information processing unit 4 in accordance with the input operations of the information processing unit 4.

To enable the measurement item resetting process, the user checks the checkbox C1. When the checkbox C1 is checked, the user selects one of three modes associated with the checkboxes C2 through C4 as the measurement item resetting process.

When the checkbox C2 is selected, many measurement items can be set for the current measurement from among the measurement items in past measurement results of the patient and measurement items input by the physician for the current measurement. When the checkbox C3 is selected, measurement items obtained by applying measurement data of past measurement results of the patient to the current re-examination rules are reset to the measurement items for the current measurement. In this case, when re-examination is determine to be unnecessary even when the measurement data of past measurement results of the patient are applied to the current re-examination rules, the measurement items are not reset and the measurements are performed according to the measurement items set by the physician in the current examination.

When the checkbox C4 is selected, the measurement items in the most recent re-examination measurement results, among the measurement data in past measurement results of the patient, are reset in the measurement items of the current measurement. In this case, when there are not any re-examination measurement results of the patient, the measurement items are not reset, and the measurement is performed according to the measurement items set by the physician in the current examination.

When either of the checkboxes C3 or C4 is selected, checkbox C5 also becomes checkable. The user checks the checkbox C5 to set the search period of past measurement results. In this case, the user can set a period of a number of days in the field R1 from the current time as the search period for the past measurement results. For example, when the checkboxes C4 and C5 are checked and [10] is entered in the field R1, the most recent re-examination measurement results are extracted from the measurement results database as the objective measurement results of the patient up to 10 days previous to the current time. When the checkbox C4 is checked but the checkbox C5 is not checked, all measurement results of the patient stored in the measurement results database are extracted as the objective the most recent re-examination measurement results.

When the checkbox C2 is checked, the user can select one or the other of two condition associated with the checkboxes C6 and C7 as the extraction condition of past measurement results to compare with the currently set measurement items. When the checkbox C6 is selected, the most recent measurement results of the patient are extracted. In this case, re-examination measurement results are included as patient measurement results in the measurement results database so that when initial examination results that are more recent than these re-examination measurement results are included as measurement results of this patient, the more recent initial examination measurement results are extracted for comparison and the initial examination measurement results are compared with the currently set measurement items. When the checkbox C7 is selected, however, the most recent re-examination measurement results of the patient are extracted. In this case, re-examination measurement results and initial examination measurement results are included as patient measurement results in the measurement result database, and re-examination measurement results are extracted for comparison even when the re-examination measurement results are old, such that the measurement items of the re-examination measurement results are compared with the currently set measurement items.

When either the checkbox C6 or C7 is selected, the user can stipulate the search period of past measurement results by checking the checkbox C8. The function of the checkbox C8 is identical to the function of the checkbox C5. That is, the user can set a period of a number of days in the field R2 from the current time as the search period for the past measurement results.

Figure 11B:
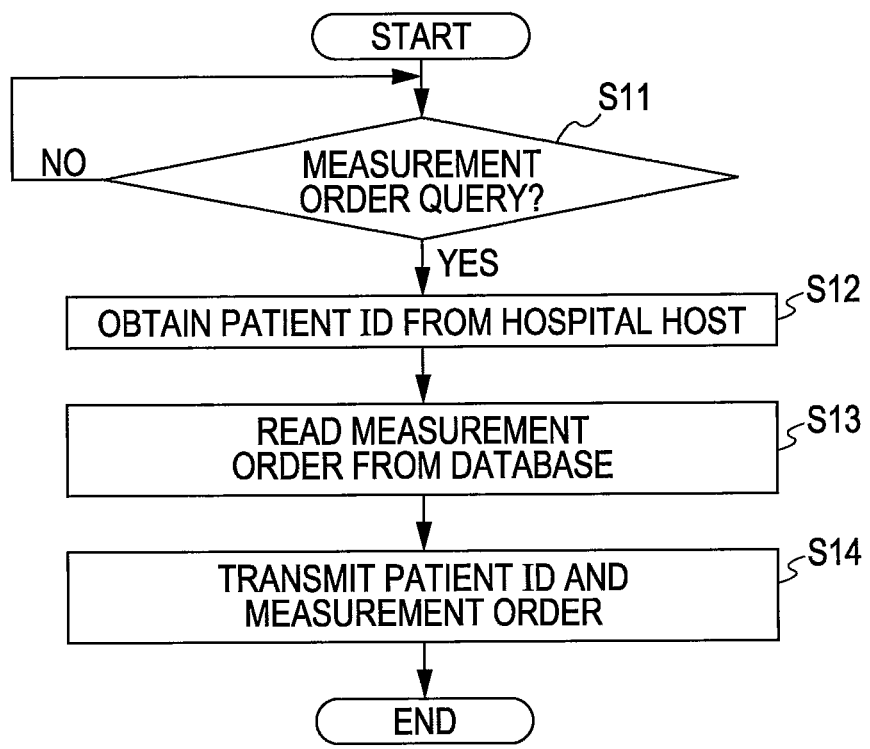

FIGS. 11(a) and 11(b) are flow charts showing the measurement item setting process. The process of FIG. 11(a) is performed by the CPU 401 of the information processing unit 4. The process of FIG. 11(b) is performed by the CPU 101 of the laboratory host 10.

Referring to FIG. 11(a), when the rack L is placed on the right table 21 (refer to FIG. 4) the sample container T is moved to the barcode reading position P2 (refer to FIG. 4), the CPU 401 controls the barcode reader B1 to read the sample ID from the barcode label T1 adhered on the sample container T (S101), and the read sample ID is associated with the holding position of the sample container T in the work list, and stored in the work list (S102). This recording process is performed for all sample containers T held in the rack L. The CPU 401 transmits the sample ID recorded in the work list to the laboratory host 10, and queries the laboratory host 10 for the measurement order (measurement items) input for each sample and the patient ID of each sample (S103).

Referring to FIG. 11(b), when the measurement order and patient ID query is received from the information processing unit 4 (S11: YES), the CPU 101 of the laboratory host 10 obtains the patient ID corresponding to each sample from the hospital host 40 (S12), and reads the measurement orders corresponding to each sample from the database itself (S13). The laboratory host 10 transmits the read measurement order and patient ID to the information processing unit 4 (S14).

Referring to FIG. 11(a), when the patient ID and measurement order corresponding to each sample is obtained from the laboratory host 10 (S104: YES), the CPU 401 associates and records the patient ID and measurement items (hereinafter referred to as "input measurement items") in the obtained measurement order in the work list (S105). Data in associated items are stored in the work list in the manner as shown in FIG. 9(a), for example. The date/time represents the time at which the patient ID and input measurement items associated with each sample were recorded. The measurement status is unmeasured in all case of this example.

When recording to the work list is completed, the CPU 401 determines whether the re-examination process is enabled via the re-examination setting screen shown in FIG. 10(b) (S106). When the re-examination process is not enabled (S106: NO), the CPU 401 executes measurement and analysis of each sample according to the input measurement items recorded on the work list in step S105 (S109).

When the re-examination process is enabled (S106: YES), however, the CPU 401 obtains the measurement items (hereinafter referred to as "revised measurement items") to be reset for the input measurement items in the work list according to which checkbox C2 through C4 of FIG. 10(b) has been selected, based on the measurement results stored in the measurement results database (S107: revised measurement items obtaining process). Revised measurement items are obtained for each sample recorded in the work list. Then the CPU 104 executes the replacement process for replacing the input measurement items recorded on the work list with the revised measurement items according to which checkbox C2 through C4 has been selected (S108: measurement item revision process). This process also is performed for each sample recorded on the work list.

After the input measurement items recorded on the work list have been replaced, the CPU 401 executes measurement and analysis of each sample according to the revised measurement items reset on the work list. When measurement of each sample is completed, the CPU 401 stores the measurement results in the measurement result database (S110). The CPU 401 then executes the re-examination process based on the current measurement results (S111). When re-examination is required, the measurement and analysis are performed according to the items requiring re-examination in the re-examination process. When the re-examination process has been performed for all samples held in the rack L, the CPU 401 ends the processing of the rack L and returns to step S101 to await the arrival of the next rack L.

Figure 12A:
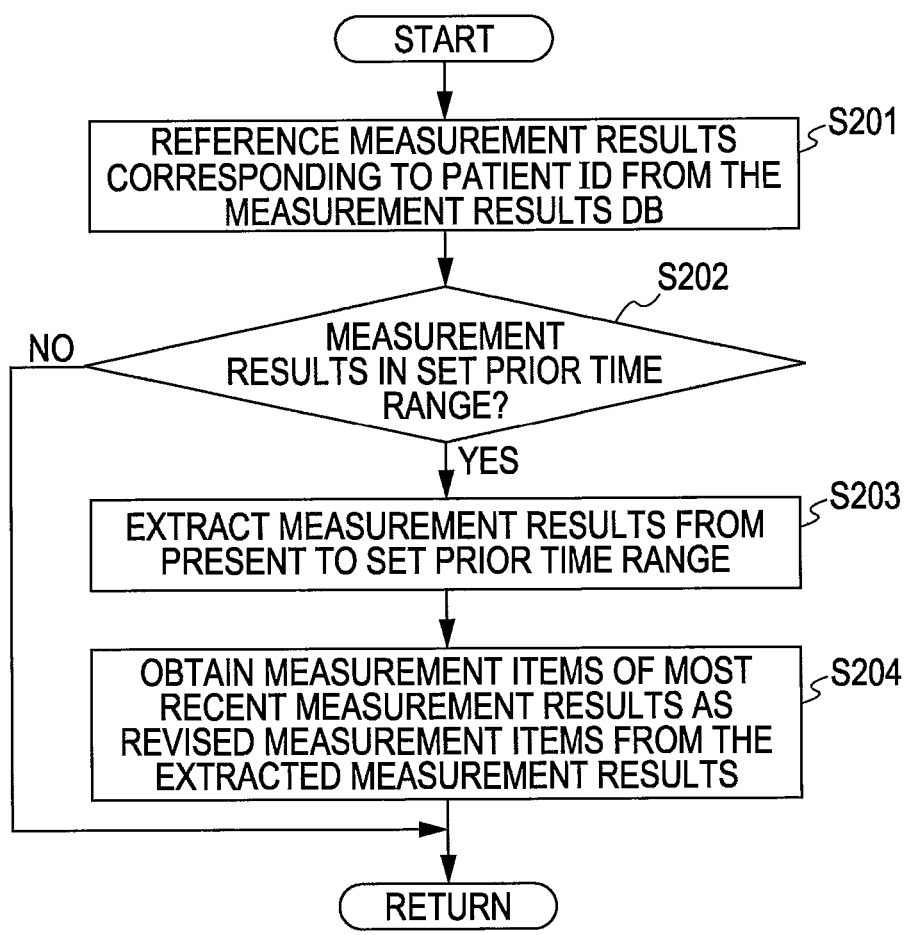
FIGS. 12A and 12B are flow charts showing the revised measurement item obtaining processes of the embodiment.
Figure 12B:
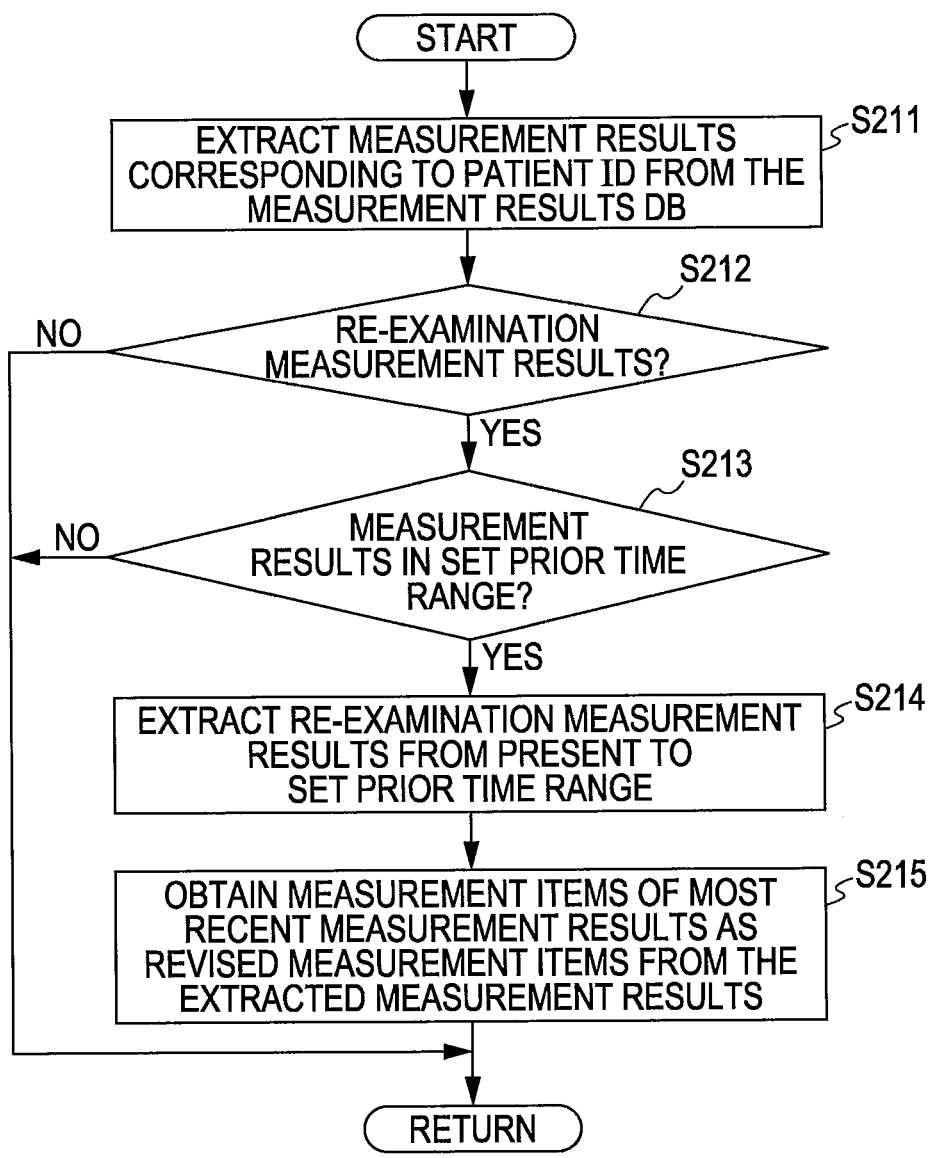
Figure 13A:
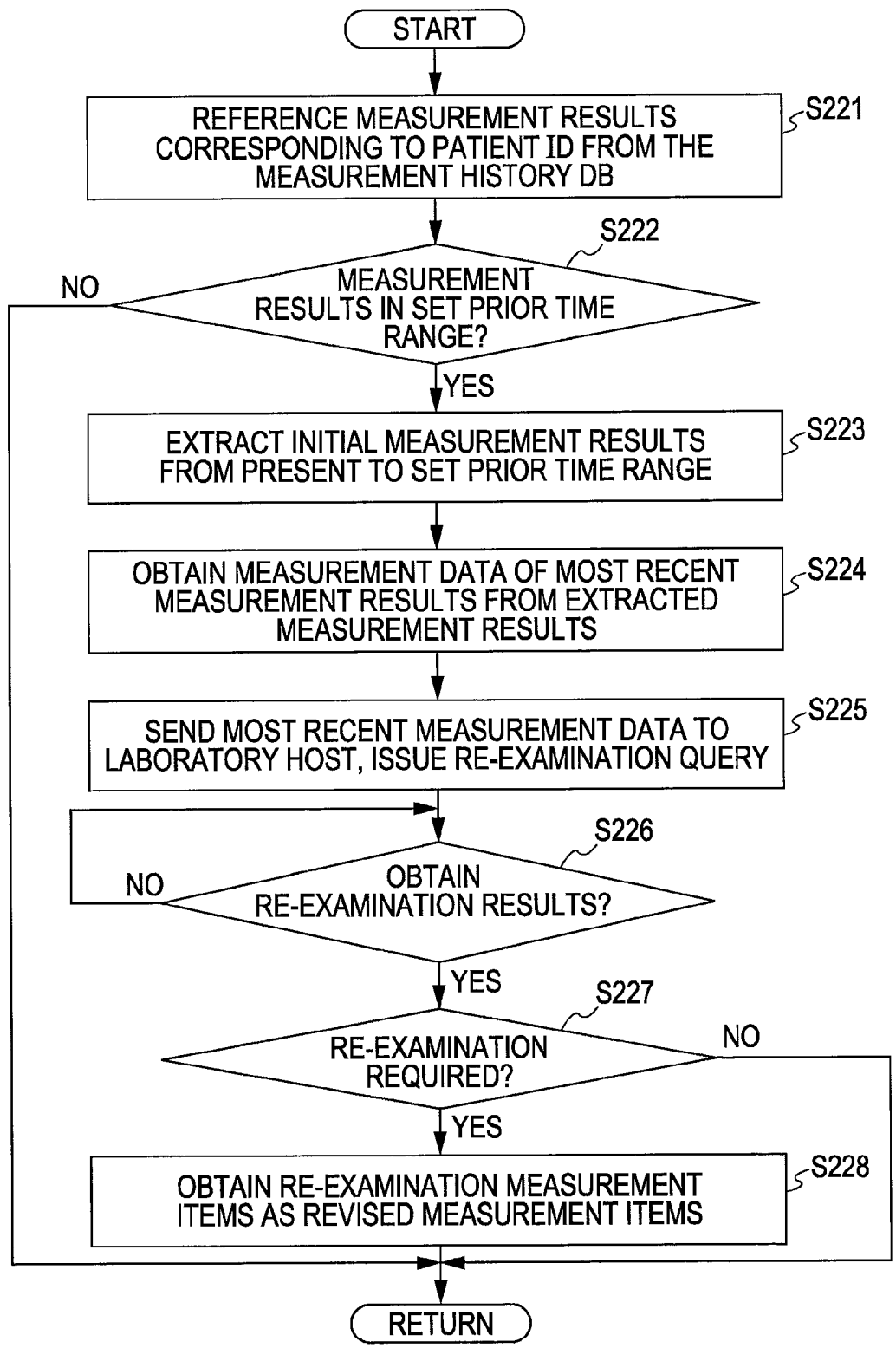
FIGS. 13A and 13B are flow charts showing the revised measurement item obtaining processes of the embodiment.

FIGS. 12(a) and (b) and 13(a) and (b) are flow charts showing the revised measurement item obtaining process executed in step S107 of FIG. 11(a). FIG. 12(a) shows the process executed when checkbox C1, C2 and C6 are selected in the setting screen of FIG. 10(b); FIG. 12(b) shows the process executed when checkbox C1, C2, and C7 or checkbox C1 and C4 are selected in the setting screen of FIG. 10(b); FIG. 13(a) shows the process executed when checkbox C1 and C3 are selected in the setting screen of FIG. 10(b). The processes in FIGS. 12(a), 12(b), and 13(a) and 13(b) are performed for all samples recorded in the work list.

When checkbox C1, C2, and C6 are selected in the setting screen of FIG. 10(b), the revised measurement items are the measurement items in the most recent measurement results among the past measurement results of the patient. In the process of FIG. 12(a), therefore, the measurement items of the most recent measurement results are obtained as the revised measurement items from among the past measurement results of the patient.

Referring to FIG. 12(a), the CPU 401 references the measurement results associated with the patient ID in the work list from among the measurement results stored in the measurement result database (S201), and determines whether measurement results exist from prior to the set time among the referenced measurement results (S202). Specifically, the CPU 401 extracts the patient ID associated with the sample ID of the sample to be measured from the work list, compares the extracted patient ID with patient IDs in the measurement result database, and sets the measurement results that match both patient IDs as extraction candidate measurement results. The CPU 401 then compares the current date with the measurement date of measurement results of the extraction candidates, and determines whether measurement results for which the measurement date is included in the period from the current date up to the set previous time are also included in the measurement results of the extraction candidates.

The set time in the process shown in FIG. 12(a) is the number of days entered in the field R2 of FIG. 10(b). When the checkbox C8 is not checked, the set time in step S202 of FIG. 12(a) becomes infinite, and a simple determination is then made as to whether the measurement results of this patient are included in the measurement results database in step S202.

When the determination is NO in step S202, the CPU 401 cannot obtain revised measurement items for the sample, and terminates the revised measurement item obtaining process. When the determination is YES in step S202, however, the CPU 401 extracts the measurement results included among the measurement results for which the measurement date is included in the period from the current date up to the set previous time from the extraction candidate measurement results (S203). The CPU 401 then obtains the measurement items of the most recent measurement results among the extracted measurement results as the revised measurement items corresponding to the sample (S204), and the revised measurement items obtaining process ends. Thus, the most recent measurement results are extracted in step S204 regardless of the earlier examinations and re-examination.

When checkbox C1 and C4 or check box C1, C2, and C7 are selected in the setting screen of FIG. 10(b), the revised measurement items becomes the measurement items in the most recent re-examination measurement results among the past measurement results of this patient. In the process of FIG. 12(b), therefore, the measurement items of the most recent re-examination measurement results are obtained as the revised measurement items from among the past measurement results of the patient.

Referring to FIG. 12(b), the CPU 401 references the measurement results associated with the patient ID in the work list from among the measurement results stored in the measurement result database (S211), and determines whether re-examination measurement results exist among the referenced measurement results (S212). Specifically, the CPU 401 extracts the patient ID associated with the sample ID of the sample to be measured from the work list, compares the extracted patient ID with patient IDs in the measurement result database, and sets the measurement results that match both patient IDs as extraction candidate measurement results. The CPU 401 then references the re-examination flag of the measurement results of a first extraction candidates, and determines whether measurement results having a re-examination flag of [1] are included in the measurement results of the first extraction candidates.

When re-examination measurement results are not included in the measurement results of the first extraction candidates (S212: NO), the CPU 401 cannot obtain the revised measurement items for this sample, and terminates the revised measurement item obtaining process. When the determination is YES in step S212, however, the CPU 401 extracts the measurement results for which the re-examination flag is [1] among the measurement results of the second extraction candidates, and determines whether measurement results up to the set previous time exist among the second extraction candidate measurement results (S213). The determination related to the time in step S213 is performed identically to the determination of step S202 of FIG. 12(a).

Note that the set time in the process shown in FIG. 12(b) is the number of days entered in the field R1 or field R2 of FIG. 10(b). When the checkbox C5 and C8 are not checked, a determination is simply made as to whether the measurement results of this patient are included in the measurement results of the second extraction candidate in step S213 of FIG. 12(b).

When the determination is NO in step S213, the CPU 401 cannot obtain revised measurement items for the sample, and terminates the revised measurement item obtaining process. When the determination is YES in step S213, however, the CPU 401 extracts the measurement results included among the measurement results for which the measurement date is included in the period from the current date up to the set previous time from the second extraction candidate measurement results (S214). The CPU 401 then obtains the measurement items of the most recent measurement results among the extracted measurement results as the revised measurement items corresponding to the sample (S215), and the revised measurement items obtaining process ends.

When the checkbox C1 and C2 are selected in the setting screen of FIG. 10(b), the revised measurement items are obtained by applying the measurement data of the earliest examination, among the past measurement data of the patient, to the current re-examination rule. In the process of FIG. 13(a), therefore, the revised measurement items are obtained by applying the measurement data of the earliest measurement results, among the past measurement results of the patient, to the current re-examination rule.

Referring to FIG. 13(a), the CPU 401 references the measurement results associated with the patient ID of the [patient recorded in the work list from among the measurement results stored in the measurement result database (S221), and determines whether measurement results exist from prior to the set time among the referenced measurement results of the patient (S222). The processes of steps S221 and S222 are identical to the processes of the steps S201 and S202 of FIG. 12(a).

The set time in the process shown in FIG. 13(a) is the number of days entered in the field R1 of FIG. 10(b). When the checkbox C5 is not selected, a determination is simply made as to whether measurement results of the patient exist in the measurement result database in step S222.

When the determination is NO in step S222, the CPU 401 cannot obtain revised measurement items for the sample, and terminates the revised measurement item obtaining process. When the determination is YES in step S222, however, the CPU 401 extracts the initial measurement results included among the measurement results for which the measurement date is included in the period from the current date up to the set previous time (S223). The CPU 401 determines whether there is an initial examination by determining whether the re-examination flag is [0] in the measurement result database. The CPU 401 then reads the measurement data of the most recent measurement results among the extracted measurement results from the measurement results database (S224), transmits the read measurement data together with the sample ID of the sample to the laboratory host 10, and issues a re-examination query relating to the measurement data (S225).

Figure 13B:
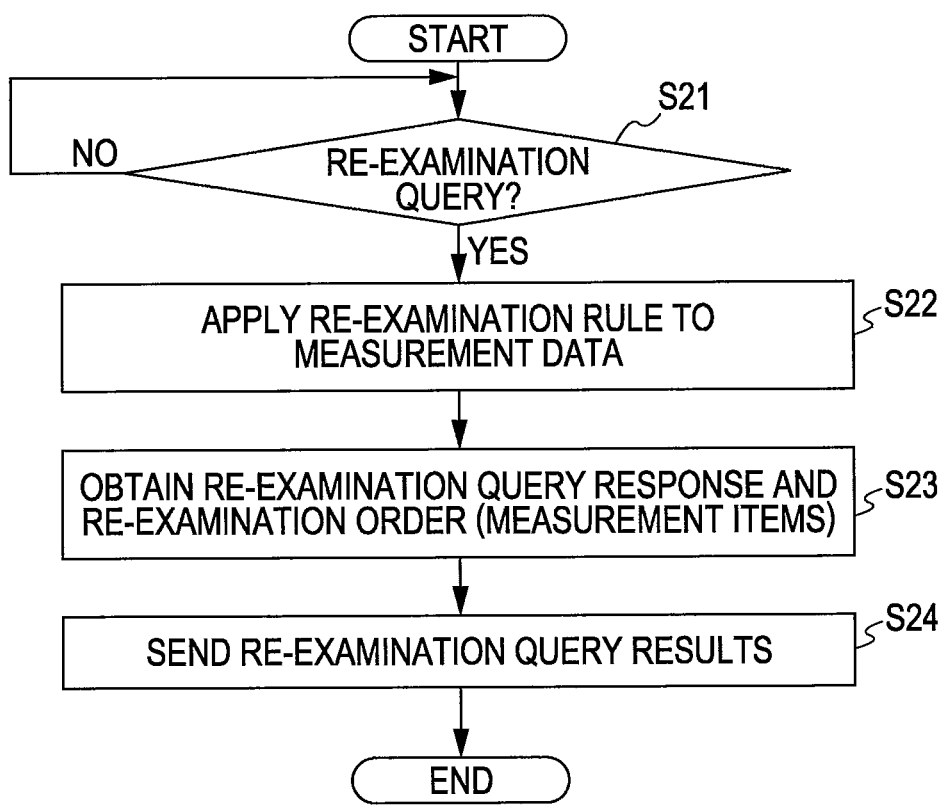

FIG. 13(b) is a flow chart showing the process in the laboratory host 10 when a re-examination query is received.

When the CPU 101 of the laboratory host 10 receives the re-examination query from the sample analyzer 1 (S21: YES), the CPU 101 applies the received measurement data to the re-examination rule stored on the hard disk 104 (S22), and obtains there-examination measurement orders and re-examination determinations (S23). The re-examination rules are configured by conditional text and results text, and measurement orders (measurement items) recorded in the results texts are acquired when the measurement data satisfy the conditions stipulated in the conditional texts. Re-examination is unnecessary when the measurement data do not satisfy the conditions stipulated by the conditional text. The CPU 101 transmits the acquired measurement orders and re-examination query results together with the sample IDs to the sample analyzer 1 (S24).

Returning to FIG. 13(a), when the CPU 401 of the sample analyzer 1 receives the measurement orders (measurement items) and re-examination query results from the laboratory host 10 (S226: YES), the CPU 401 determines whether re-examination is required from the received re-examination query results (S227). When re-examination is unnecessary (S227: NO), the CPU 401 cannot obtain the revised measurement items for the sample, and terminates the revised measurement item obtaining process. When re-examination is required (S227: YES), however, the CPU 401 obtains the measurement items included in the re-examination measurement order received from the laboratory host 10 as the revised measurement items for the sample (S228), and the revised measurement item obtaining process ends.

Figure 14A:
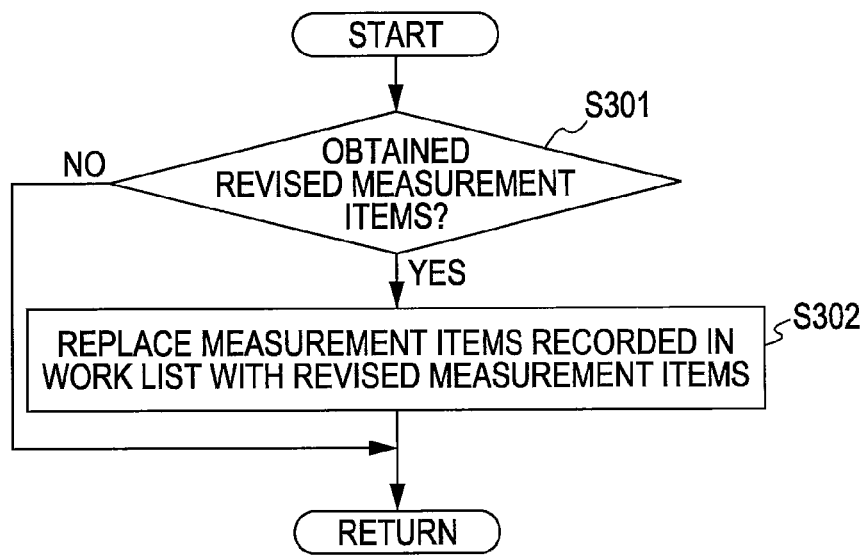
FIGS. 14A and 14B are flow charts showing the revised measurement item obtaining processes of the embodiment.
Figure 14B:
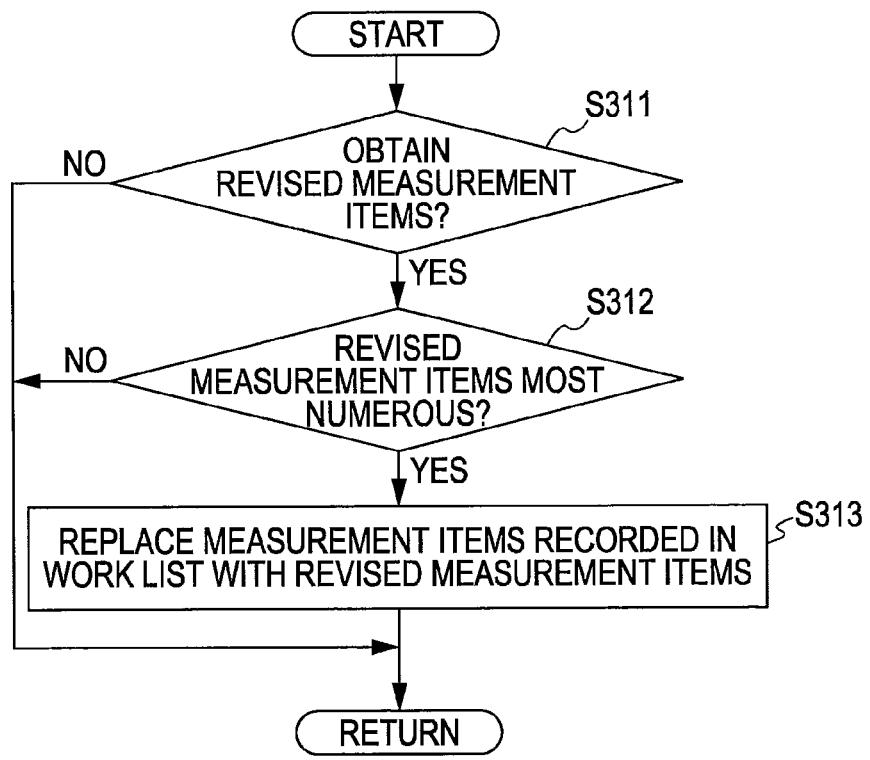

FIGS. 14(a) and (b) are flow charts showing the measurement item revision process executed in step S108 of FIG. 11(a). FIG. 14(a) shows the process executed when either checkbox C3 or C4 is selected in the setting screen of FIG. 10(b). FIG. 14(b) shows the process executed when checkbox Cs is selected in the setting screen of FIG. 10(b). The processes in FIGS. 14(a) and 14(b) are performed for all samples recorded in the work list.

When either checkbox C3 or C4 is selected in the setting screen of FIG. 10(b), the input measurement items are replaced by the revised measurement items and used in the measurement of the sample. In the process of FIG. 14(a), therefore, a process is performed to replace the input measurement items recorded in the work list with the revised measurement items.

Referring to FIG. 14(a), the CPU 401 determines whether revised measurement items have been obtained for the sample to be measured recorded in the work list (S301). When revised measurement items are not obtained (S301: NO), the CPU 401 cannot reset the input measurement items related to the sample recorded in the work list, and the measurement items revision process is terminated. In this case, the sample is measured and analyzed according to the input measurement items in step S109 of FIG. 11(a). When revised measurement items are obtained (S301: YES), however, the CPU 401 replaces the input measurement items for the sample recorded in the work list with the obtained revised measurement items (S302). In this case, the sample is measured and analyzed according to the revised measurement items in step S109 of FIG. 11(a).

When the checkbox C2 is selected in the setting screen of FIG. 10(b), the most numerous measurement items among the input measurement items and the revised measurement items are used to measure the sample. The process of FIG. 14(b), therefore, is a process for determining measurement items by comparing the revised measurement items and the input measurement items recorded in the work list.

Referring to FIG. 14(b), the CPU 401 determines whether revised measurement items have been obtained for the sample to be measured recorded in the work list (S311). When revised measurement items are not obtained (S311: NO), the CPU 401 cannot reset the input measurement items related to the sample recorded in the work list, and the measurement items revision process is terminated. In this case, the sample is measured and analyzed according to the input measurement items in step S109 of FIG. 11(a).

When revised measurement items are obtained (S311: YES), however, the CPU 401 compares the number of revised measurement items obtained in the above process with the number of input measurement items for the sample recorded in the work list; and when the number of revised measurement items is greater than the number of input measurement items (S312: YES), the input measurement items recorded in the work list are replaced with the revised measurement items (S313). In this case, the sample is measured and analyzed according to the revised measurement items in step S109 of FIG. 11(a). When the number of revised measurement items is fewer than the number of input measurement items (S312: NO), however, the CPU 401 cannot reset the input measurement items recorded in the work list and the measurement item revision process is terminated.

Referring to FIG. 8, when the input measurement items of a sample are CBC+DIFF channels and the revised measurement items obtained by the above process are CBC+DIFF+RET channels, the input measurement items recorded in the work list are replaced by the revised measurement items because the revised measurement items are more numerous. In this case, measurements are performed for the measurement items of the CBC+DIFF+RET channels. However, when the input measurement items of a sample are CBC+DIFF+RET+PLT-F+WPC channels and the revised measurement items obtained by the above process are CBC+RET+PLT-F+WPC channels, the input measurement items recorded in the work list are not replaced by the revised measurement items because the input measurement items are more numerous. In this case, measurements are performed for the measurement items of the CBC+DIFF+RET+PLT-F+WPC channels.

When the process of FIG. 14(a) or 14(b) is executed, the work list is reset, for example, from the state shown in FIG. 9(a) to the state shown in FIG. 9(b). In this case, revised measurement items are obtained for the samples in holder positions 2, 6, and 9 of the rack L, and the measurement items of these samples are reset to the revised measurement items. The recorded date and time of the holding positions 2, 6, and 9 is changed to the date and time at which the input measurement items were replaced by the revised measurement items. When the measurements are performed according to the reset work list, the samples at the holder positions 2, 6, and 9 are measured according to the revised measurement items and the samples at the other holder positions are measured according to the input measurement items.

FIG. 15 is a flow chart showing the re-examination process performed in step S111 of FIG. 11.

When the measurement data are obtained for each sample in the process of step S110 of FIG. 11, the CPU 401 transmits the obtained measurement data together with the sample IDs to the laboratory host 10, and issues a re-examination query regarding the measurement data (S401). The laboratory host 10 therefore performs the process of FIG. 13(b), and transmits the re-examination query results and the measurement data to the sample analyzer 1.

When the CPU 401 receives the re-examination query results and the measurement data from the laboratory host 10 (S402: YES), the CPU 401 determines whether re-examination is required based on the received re-examination query results (S403). When re-examination is unnecessary (S403: NO), the CPU 401 terminates the process. When re-examination is required (S403: YES), however, the CPU 401 measures and analyses of the samples according to the measurement order for re-examination received from the laboratory host 10 (S404), and stores the measurement results in the measurement results database (S405). In this case the re-examination flag is set to [1] in the measurement results. The measurement results are referenced in the next measurement for this patient.

According to this embodiment appropriate measurement items for the patient are measured and analyzed via a sample by reflecting the past measurement results for the same patient in the measurement items of the current measurements. As a result, more appropriate analytical results are obtained.

According to the present embodiment, the most appropriate measurement items can be set for a sample since the current measurement items can be set based on the measurement items of the most recent prior measurement by selecting any of the checkboxes C4, C6, C7 in the setting screen of FIG. 10(b).

According to the present embodiment, the most appropriate measurement items can be set for a sample since the current measurement items can be set based on the measurement items used in past re-examinations by selecting any of the checkboxes C4, C6, C7 in the setting screen of FIG. 10(b).

According to the present embodiment, when the measurement rules of the re-examination determination stored in the laboratory host 10 are changed from those of the previous measurement, the previous measurement results can be applied to the new determination rules to obtained measurement items for the re-examination and which can then be set as the current measurement items by selecting the checkbox C3 in the setting screen of FIG. 10(b). As a result, appropriate measurement items can be set for the sample.

According to the present embodiment, since the resetting process can be enabled and disabled in the setting screen of FIG. 10(b) by suitably selecting either via the checkbox C1, the user can disable the resetting process by removing the check from the checkbox C1 when measurement and analysis is desirable using the actually input measurement items rather than measurement items based on past measurement results. As a result, convenience for the user is increased.

According to the present embodiment, the user can use a suitable and preferred method for the resetting process according to the sample measurement frequency and condition of the patient since the method used for the resetting process can be suitably selected from among choices of a plurality of types in the setting screen of FIG. 10(b).

Note that the measurement items based on the past measurement results obtained at widely divergent times will usually not be suitable for the current measurements since the condition of the patient and the behavior of the sample will change over time. According to the present embodiment, reflecting measurement items from measurements that are too old in the current measurement can be avoided because the temporal acquisition range of the revised measurement items can be limited to a predetermined time prior to the present time in the setting screen of FIG. 10(b).

According to the present embodiment, The temporal acquisition range of the revised measurement items can be set via the input in the fields R1 and R2 in the setting screen of FIG. 10(b). As a result, for example, the user can dynamically change the temporal acquisition range of the revised measurement items while considering the frequency with which the patient is examined. Hence, convenience for the user is increased.

According to the present embodiment, measurement results that normally must be obtained can actually be obtained when either the input measurement items or the revised measurement items are applied to the measurement of a sample since the measurement items of the CBC channel must be selected when setting of the measurement items as shown in FIG. 8(b).

First Modification

Although revised measurement items are obtained in the information processing unit 4 in the present embodiment, revised measurement items also may be obtained in the laboratory host 10. In this case the measurement results data are stored on the hard disk 104 of the laboratory host 10.

Figure 16A:
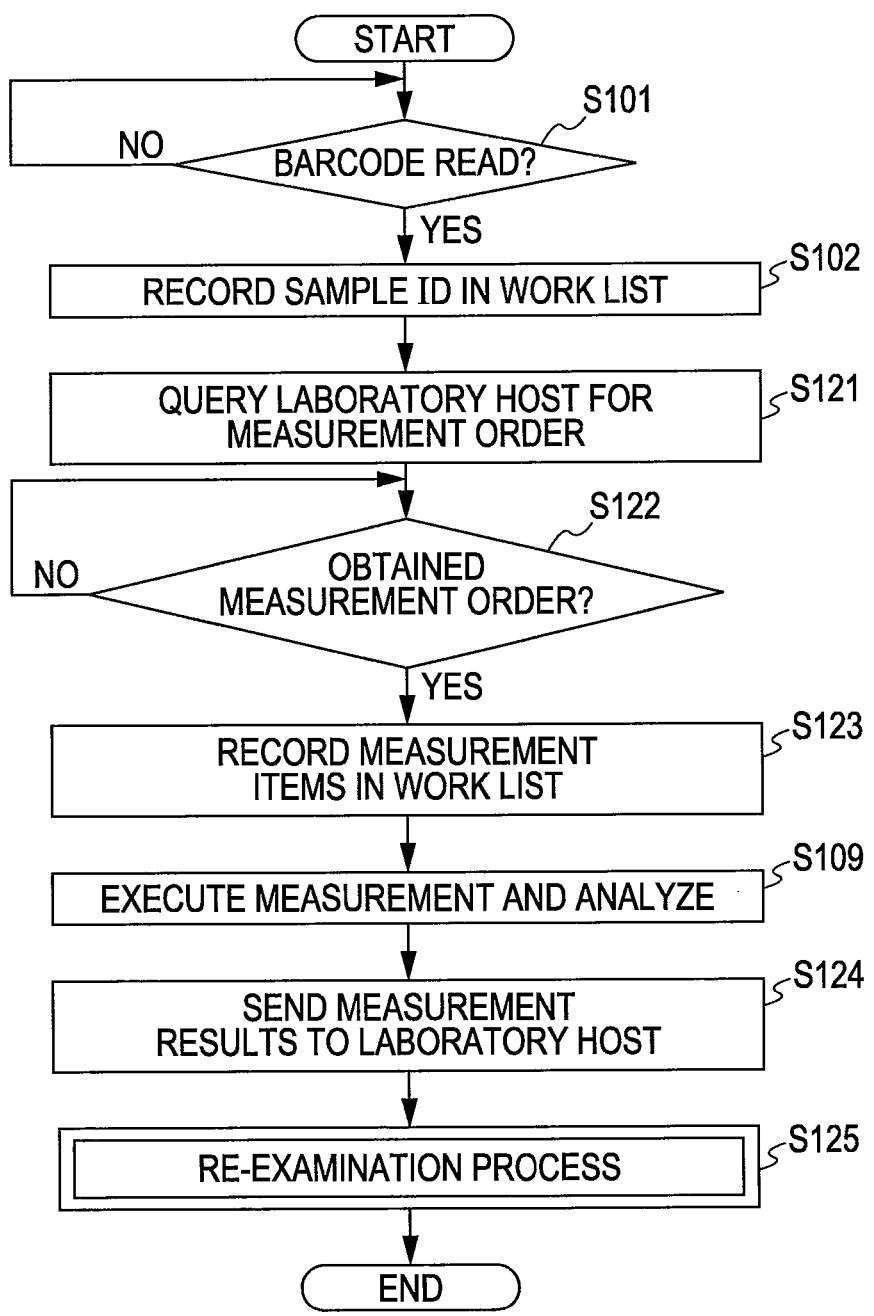
FIGS. 16A and 16B are flow charts showing the re-examination process and the measurement item setting process of the information processing unit of a first modification.
Figure 16B:
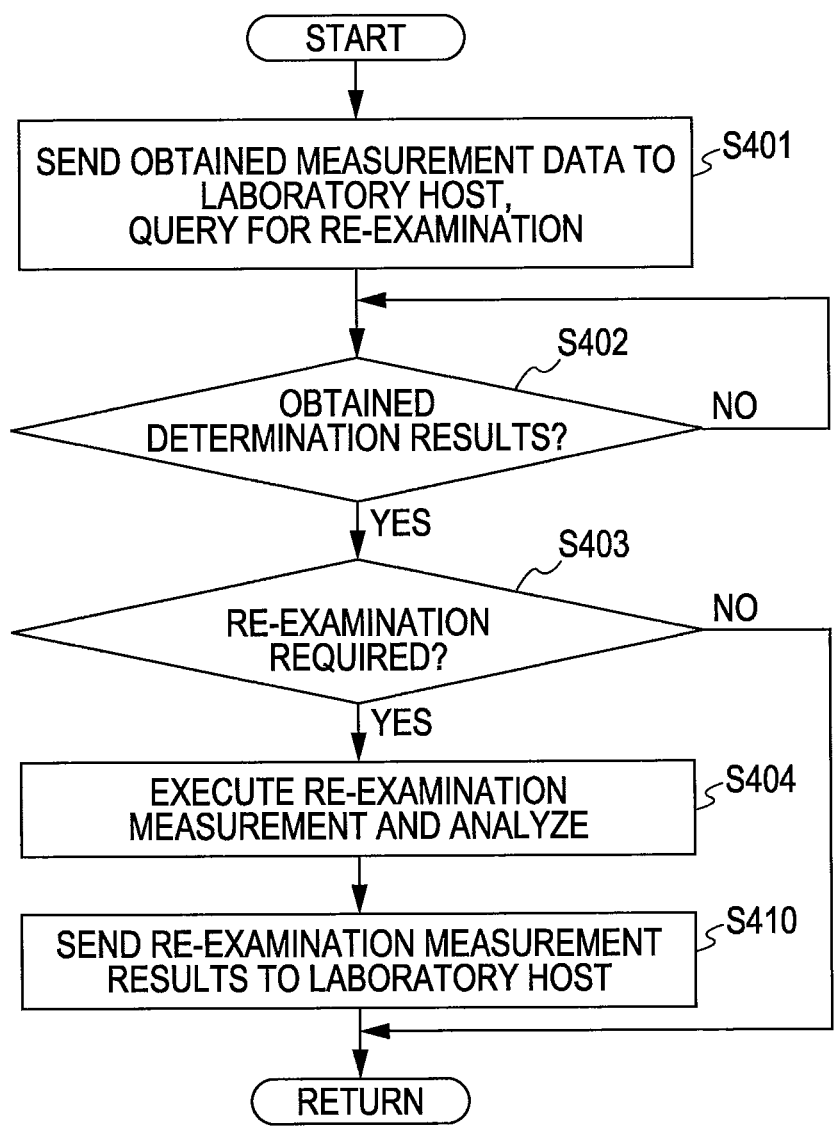

FIG. 16(*a*) is a flow chart showing the process performed in the information processing unit 4 in this case. In the process of FIG. 16(*a*), measurements and analyses are performed according to the measurement order (measurement items) simply obtained from the laboratory host 10 without performing the resetting process. When a measurement is performed, the measurement results are transmitted from the information processing unit 4 to the laboratory host 10 because the measurement results are managed in the measurement results database on the laboratory host 10 side.

Referring to FIG. 16(*a*), when the sample ID of each sample held in the rack L has been recorded in the work list via a process identical to that of steps S101 and S102 of FIG. 11(*a*), the CPU 401 transmits the sample IDs recorded in the work list to the laboratory host 10 and queries the laboratory host 10 concerning the measurement order (measurement items) of each sample (S121). Thereafter, when the measurement order of each sample is obtained from the laboratory host 10 (S122: YES), the CPU 401 associates and records the sample ID and corresponding measurement items in the obtained measurement order (S123). When the recording to the work list is completed, the CPU 401 executes measurement and analysis for each sample according to the input measurement items recorded in the work list (S109). Then when the measurement of each sample is completed, the CPU 401 transmits the measurement results together with the sample ID to the laboratory host 10 (S124). The received measurement results are stored in the analysis results database on the laboratory host 10 side. The CPU 401 then executes the re-examination process based on the current measurement results (S125). When re-examination is required, the measurement and analysis are performed according to the items requiring re-examination in the re-examination process.

FIG. 16(*b*) is a flow chart showing the re-examination process executed in step S125). This flow chart differs from the flow chart of FIG. 15 only in regards to step S410. That is, when performing the re-examination measurements, the CPU 401 transmits the measurement results together with the sample ID to the laboratory host 10 (S410). The received measurement results are stored in the analysis results database on the laboratory host 10 side. At this time the re-examination flag is set to [1] in the measurement results.

Figure 17B:
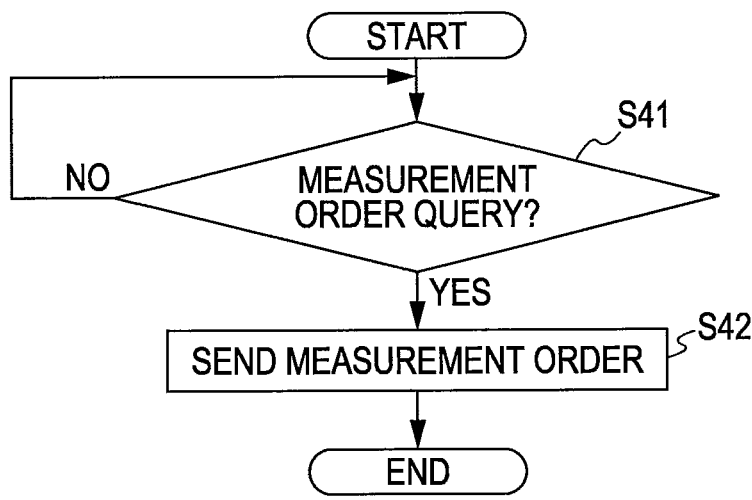
Figure 17C:
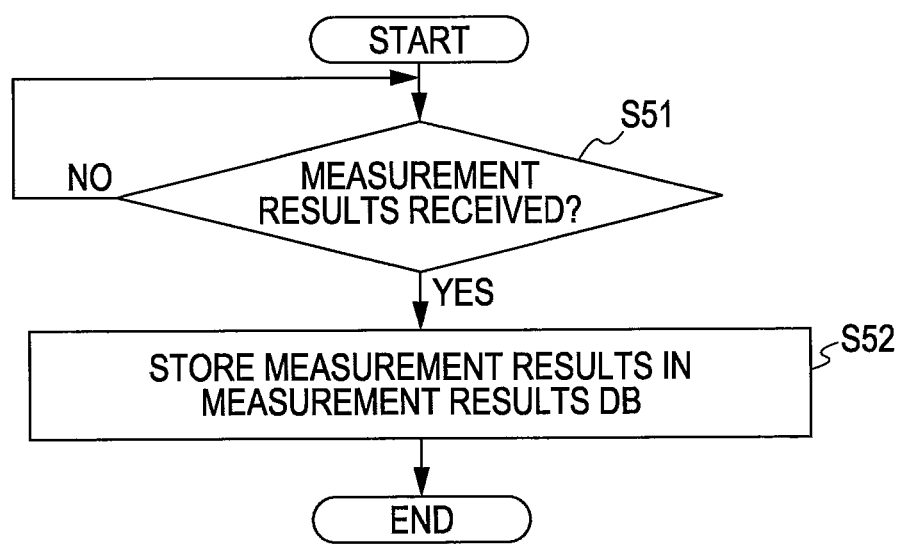

FIG. 17(*a*) shows the measurement item setting process in the laboratory host 10.

When the CPU 101 of the laboratory host 10 obtains the measurement order and sample ID from the hospital host 40 (S31: YES), the obtained measurement order and sample ID are recorded in the measurement order list on the hard disk 104. The measurement order list has the same structure as the work list shown in FIG. 9(*a*). The CPU 101 then determines whether resetting of the measurement items is enabled (S33). The laboratory host 10 can enable/disable the resetting process and the content of the resetting process via the setting screen of FIG. 10(*b*) similar to the previous embodiment.

When the resetting process is disabled (S33: NO), the CPU 101 terminates the setting of the measurement items related to the sample ID. When the resetting process is enabled (S33: YES), the CPU 101 obtains the patient ID corresponding to the sample ID from the hospital host 40 and records the obtained patient ID in the measurement order list in the same way as in step S12 of FIG. 11(*b*) (S34). Thereafter, the CPU 101 references the measurement results database stored on the hard disk 104, and executes the revised measurement item obtaining process (S35) and revised measurement item revision process (S36). The revised measurement item obtaining process (S35) and revised measurement item revision process (S36) are identical processes to steps S107 and S108 of FIG. 11(*a*), respectively. That is, in steps S107 and S108, the processes of any among FIG. 12 through 14 are performed via the content set through the setting screen of FIG. 10(*b*) similar to the previous embodiment. Note that since the re-examination rule is stored on the hard disk 104 on the laboratory host 10 side, steps S22 and S23 of FIG. 13(*b*) are executed to obtain the re-examination query result in place of step S225 of FIG. 13(*a*), which is omitted.

The measurement items in the measurement order recorded in the measurement order list can be suitably replaced by the revised measurement items via the processes of steps S35 and S36 of FIG. 17(*a*). Therefore, when the measurement items of a predetermined sample in the measurement order list are replaced with the revised measurement items and a measurement order transmission request for the sample is issued by the sample analyzer 1 in step S121 of FIG. 16(*a*), the measurement order including the revised measurement items is transmitted to the sample analyzer 1.

FIG. 17(*b*) is a flow chart showing the measurement order transmission process executed by the laboratory host 10. FIG. 17(*c*) is a flow chart showing the measurement result storage process executed by the laboratory host 10.

Referring to FIG. 17(*b*), When the CPU 101 of the laboratory host 10 receives the measurement order transmission request and sample ID from the sample analyzer 1 (S41: YES), the measurement order corresponding to the received sample ID is obtained from the measurement order list stored on the hard disk 104, and the obtained measurement order is then transmitted to the sample analyzer 1 (S42).

Referring to FIG. 17(*c*), when the CPU 101 of the laboratory host 10 receives the sample ID and measurement results from the sample analyzer 1 (S51: YES), the patient ID corresponding to the received sample ID is read from the measurement order list, and the received measurement results and the read patient ID are stored in the measurement results database on the hard disk 104 (S52).

According to this embodiment appropriate measurement items for the patient are measured and analyzed via a sample by reflecting the past measurement results for the same patient in the measurement items of the current measurements similar to the previous embodiment. As a result, more appropriate analytical results are obtained.

Second Modification

Although the re-examination rules are stored on the laboratory host 10 side in the above embodiment, the re-examination rules also may be stored on the hard disk 404 of the information processing unit 4. In this case the processes of FIG. 13(*a*) are revised ash shown in FIG. 18(*a*). In the flow chart of FIG. 18(*a*), step S225 of FIG. 13(*a*) is replaced by step S230. In step S230, the processes of steps S22 and S23 of FIG. 13(*b*) are performed. That is, the CPU 401 applies the re-examination rule stored on the hard disk 404 to the measurement order obtained in step S224, to obtain a re-examination query determination result and a measurement order to be used in re-examination.

Figure 18A:
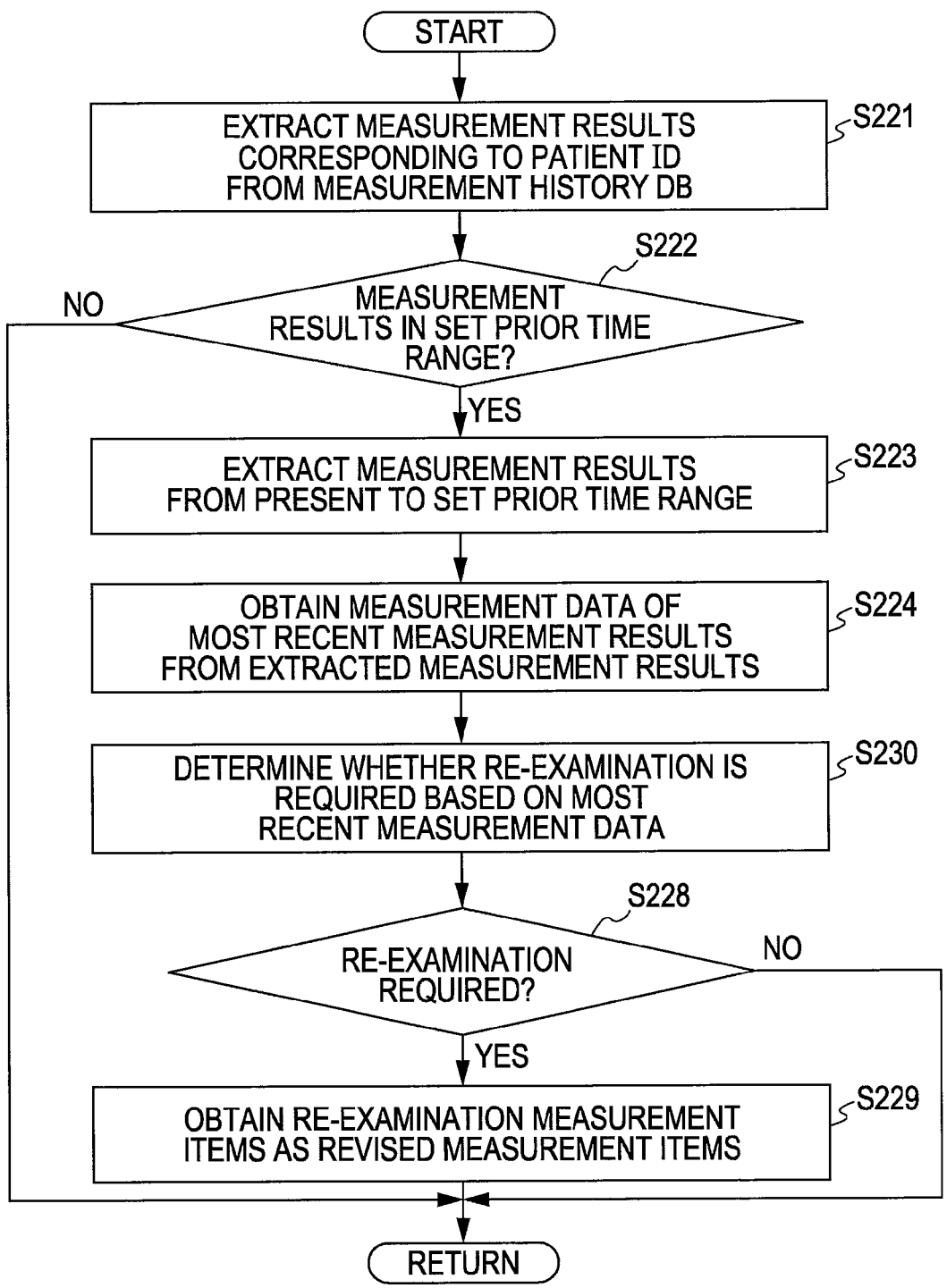
FIGS. 18A and 18B are flow charts showing the revised order obtaining processes of a second modification.
Figure 18B:
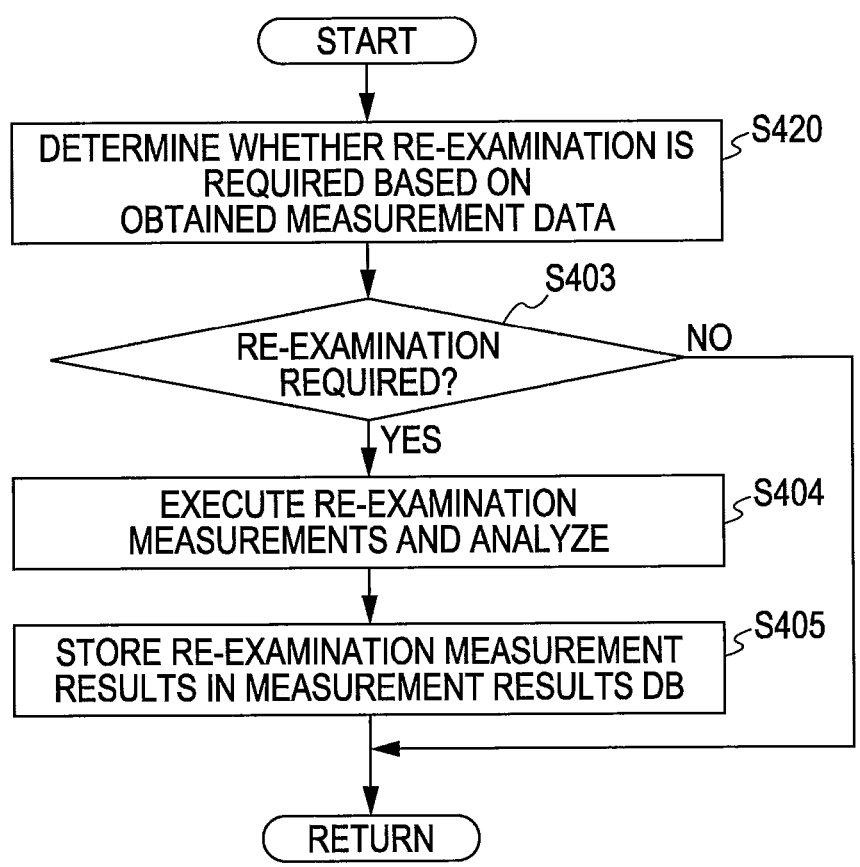

The re-examination process in step S111 of FIG. 11(*a*) is revised as shown in FIG. 18(*b*). In this case the CPU 401 applies the re-examination rule stored on the hard disk 404 to the measurement order obtained in step S109 of FIG. 11 to obtain a re-examination query determination result and a measurement order to be used in re-examination.

Although the present invention has been described above by way of an embodiment and modifications, the present invention is not limited to the embodiment or modifications.

For example, although the above embodiment is described by way of example of blood as an object to be measured, urine also be used as an object to be measured. That is, the present invention also is applicable to sample analyzers for examining urine. The present invention is further applicable to clinical sample analyzers for examining other clinical samples.

Although the rules shown on the setting screen in FIG. 10(b) are suggested as rules for the resetting processing the above embodiment, the present invention is not limited to these rules for the resetting process since other rules also may be used insofar as the past measurement results of the same patient are reflected in the measurement items of the current measurement. Among the rules shown on the setting screen in FIG. 10(b), for example, part of the condition such as the condition of checkbox C6 may be omitted from the setting screen. The rules for the re-examination process also may be set to limit the extraction range of the revised measurement items to use only a range of useful re-examination measurement results as the past measurement results. In this case, the initial measurement results among the past measurement results of the patient must be applied to the re-examination rules in the resetting process associated with the checkbox C3 of FIG. 10(b).

Measurement items are not limited to the items shown in FIG. 8(a), and other measurement items may be added or specific measurement items may be removed. Items included in the work list and the measurement results database are not limited to the items shown in FIG. 9(a) and FIG. 10(a), and may be variously modified within a range which allows implementation of a resetting process of the measurement items.

The sample ID obtaining mode also may be implemented by barcode reader, or a storage medium such as RFID or the like. The structure of the network system is not limited to the structure shown in FIG. 1 inasmuch as the hospital host 40 may be eliminated or other systems may be used.

Note that the patient ID may be obtained from a host computer installed outside the sample analyzer 1, and a user also may directly input the patient ID in the sample analyzer 1.

The rules of the resetting process also may be stored on an external host computer. In this case the sample analyzer 1 transmits the past measurement results of the patient to the host computer, and obtains the re-examination measurement items corresponding to the patient from the host computer.

Note that the embodiment of the present invention is not limited to the above described embodiments and may be variously modified insofar as such modification are within the scope of the claims.

What is claimed is:

1. A sample analyzer comprising:
a measurement device comprising an aspirating section configured to aspirate a sample contained in a sample container and a detector operable to measure the sample aspirated by the aspirating section on a plurality of measurement items;
wherein a measurement item is defined by a measurement object, a detection unit used for measurement, and a reagent such that measurement items for an identical measurement object differ based on the detection unit used for measurement and/or the reagent;
a barcode reader operable to obtain identification information of the sample contained in the sample container;
a transporting device arranged adjacent to the measurement device and the barcode reader and comprising a belt operable to transport the sample container to the measurement device for measurement and the barcode reader for identification;
an information processing device in communication with the measurement device and comprising a processor, a memory storing application programs and a display, the processor operable to execute an application program for enabling a measurement item re-setting process to perform instructions comprising:
displaying a setting screen on the display, the setting screen configured to select whether a measurement item re-setting process is enabled or not; and
receiving the selection of whether the measurement item re-setting process is enabled or not;
wherein the processor is further operable to execute an application program for setting the measurement items of the sample to perform instructions comprising:
receiving identification information of a selected sample collected from a selected subject from the barcode reader;
receiving a measurement order which has been set for the identification information of the selected sample and designates measurement items of the sample, based on the identification information of the selected sample;
determining whether the measurement item re-setting process has been enabled or not;
responsive to a determination that the measurement item re-setting process has not been enabled;
setting the currently designated measurement items in the obtained measurement order; and
controlling the measurement device to measure the selected sample on the currently designated measurement items; and
responsive to a determination that the measurement item re-setting process has been enabled;
obtaining historical measurement information which includes past measurement results of a the selected subject, the past measurement results including a plurality of past measurement items;
determining whether the past measurement items contain one or more measurement items other than the currently designated measurement items or not;
responsive to a determination that the past measurement items contain one or more measurement items other than the currently designated measurement items;
setting new measurement items for the selected sample having a larger number than the currently designated measurement items based on the obtained historical measurement information; and
controlling the measurement device to measure the selected sample on the newly set measurement items;
responsive to a determination that the past measurement items do not contain one or more measurement items other than the currently designated measurement items;
setting the currently designated measurement items; and
controlling the measurement device to measure the selected sample on the currently designated measurement items.

2. The sample analyzer of claim 1, wherein the barcode reader comprises a reading section that reads information including the identification information of each sample from a medium attached to each sample container.

3. The sample analyzer of claim 1, further comprising:
a measurement history database that stores the past measurement results of the selected subject in association with the identification information of the selected sample,
wherein the instruction of obtaining historical measurement information further comprises:
obtaining identification information of the selected subject corresponding to the identification information of the selected sample obtained from the barcode reader;
extracting, from the measurement history database, the past measurement results corresponding to the obtained identification information of the selected subject; and
obtaining historical measurement information based on the extracted past measurement results.

4. The sample analyzer of claim 3, further comprising:
a communication unit that communicates with an external host computer,
wherein the instruction of obtaining the identification information of the selected subject comprises obtaining the identification information from the external host computer through the communication unit.

5. The sample analyzer of claim 1, wherein instruction of setting the new measurement items comprises setting, as the new measurement items, the past measurement items of a most recent measurement result among the plurality of past measurement results of the selected subject.

6. The sample analyzer of claim 1, wherein instruction of setting the new measurement items comprises setting, as the new measurement items, the past measurement items of a most recent measurement result among re-examination measurements results when the past measurement results of the selected subject includes information related to initial measurement results and information related to the re-examination measurements results.

7. The sample analyzer of claim 1, wherein
the past measurement results include the past measurement items and past measurement data corresponding to the past measurement items, and
the instruction of setting the new measurement items comprises setting, as the new measurement items, re-examination measurement items obtained by applying the past measurement data of the selected subject to a current re-examination determination rule.

8. The sample analyzer of claim 7, wherein the memory further stores the current re-examination determination rule.

9. The sample analyzer of claim 1, wherein the instruction of setting the new measurement items comprises setting, as the new measurement items, the past measurement items included in the past measurement results by replacing the designated measurement items contained in the measurement order when historical measurement information is obtained.

10. The sample analyzer of claim 1,
wherein the instruction of setting the new measurement items comprises setting, as the new measurement items, the past measurement items included in the past measurement results by replacing the designated measurement items in the measurement order when the number of the designated measurement items in the measurement order is less than the number of the past measurement items included in the past measurement results; and setting, as the new measurement items, the designated measurement items included in the measurement order when the number of designated measurement items in the measurement order is greater than the number of the past measurement items included in the past measurement results.

11. The sample analyzer of claim 1, wherein the instruction of obtaining historical measurement information further comprises obtaining the historical measurement information using the measurement result during a predetermined time frame ranging from a current time among the past measurement results.

12. The sample analyzer of claim 11, wherein the processor is configured to set the predetermined time frame.

13. The sample analyzer of claim 1, wherein the past measurement items included in the historical measurement information and the designated measurement items included in the measurement order include basic measurement items in common;
wherein the basic measurement items in common comprise white blood cells, red blood cells, platelets, and hemoglobin.

14. The sample analyzer of claim 1, wherein the sample analyzer is a blood cell counter; and the measurement section measures blood samples.

15. The sample analyzer of claim 1, wherein the setting screen is configured to select one measurement item re-setting rule from a plurality of measurement item re-setting rules.

16. The sample analyzer of claim 1, wherein the measurement device comprises a second barcode reader that is arranged in the measurement device and is operable to obtain identification information of the sample contained in the sample container that is transported by the transporting device.

17. The sample analyzer of claim 1, wherein the new measurement items include the one or more measurement items and the currently designated measurement items.

18. A sample analyzer comprising:
a measurement device comprising an aspirating section configured to aspirate a blood sample contained in a sample container and a detector operable to measure blood cells in the sample aspirated by the aspirating section on a plurality of measurement items;
a barcode reader operable to obtain identification information of the sample contained in the sample container;
a transporting device arranged adjacent to the measurement device and the barcode reader and comprising a belt operable to transport the sample container to the measurement device and the barcode reader; and
an information processing device in communication with the measurement device and comprising a processor, a memory storing application programs, the processor operable to execute an application program for setting the measurement items of the sample to perform instructions, comprising:
receiving identification information of a selected sample collected from a selected subject from the barcode reader;
receiving a measurement order which has been set for the identification information of the selected sample and designates measurement items of the sample, based on the identification information of the sample;
determining whether a measurement item re-setting process is enabled or not;

responsive to a determination that the measurement item re-setting process is not enabled;
    setting the designated measurement items in the measurement order; and
    controlling the measurement device to measure the selected sample on the designated measurement items; and responsive to a determination that the measurement item re-setting process is enabled;
    obtaining historical measurement information which includes past measurement results of the subject, the past measurement results including a plurality of past measurement items;
    determining whether the past measurement items contain a different measurement item other than the designated measurement items or not;

responsive to a determination that the past measurement items contain the different measurement item;
    setting new measurement items having a larger number than the designated measurement items based on the obtained historical measurement information; and
    controlling the measurement device to measure the selected sample on the newly set measurement items; and responsive to a determination that the past measurement items do not contain the different measurement item;
    setting the designated measurement items; and
    controlling the measurement device to measure the selected sample on the designated measurement items.

19. The sample analyzer of claim 18, wherein the new measurement items include the different measurement item and the designated measurement items.

20. The sample analyzer of claim 18, wherein the memory stores a setting whether a measurement item re-setting process is enabled or not.

21. The sample analyzer of claim 18, wherein the sample analyzer is a blood cell counter; and the measurement section measures blood samples.

\* \* \* \* \*

UNITED STATES PATENT AND TRADEMARK OFFICE
CERTIFICATE OF CORRECTION

PATENT NO.          : 9,513,282 B2
APPLICATION NO.     : 13/785703
DATED               : December 6, 2016
INVENTOR(S)         : Takuma Katou et al.

It is certified that error appears in the above-identified patent and that said Letters Patent is hereby corrected as shown below:

In the Claims

In Column 22, Claim 1, Line 41, after "measurement results of" delete "a".

In Column 22, Claim 1, Lines 51-52, after "new measurement items" delete "for the selected sample".

Signed and Sealed this
Twenty-seventh Day of June, 2017

Joseph Matal
*Performing the Functions and Duties of the*
*Under Secretary of Commerce for Intellectual Property and*
*Director of the United States Patent and Trademark Office*